(12) United States Patent
Davis et al.

(10) Patent No.: US 8,637,711 B2
(45) Date of Patent: Jan. 28, 2014

(54) SELECTIVE AND SPECIFIC PREPARATION OF DISCRETE PEG COMPOUNDS

(75) Inventors: Paul D. Davis, Dublin, OH (US); Edward C. Crapps, Philadelphia, PA (US)

(73) Assignee: Quanta BioDesign, Ltd., Powell, OH (US)

( * ) Notice: Subject to any disclaimer, the term of this patent is extended or adjusted under 35 U.S.C. 154(b) by 419 days.

(21) Appl. No.: 13/014,789

(22) Filed: Jan. 27, 2011

(65) Prior Publication Data

US 2011/0124844 A1    May 26, 2011

Related U.S. Application Data

(62) Division of application No. 11/203,950, filed as application No. PCT/US2004/004274 on Feb. 13, 2004, now Pat. No. 7,888,536.

(60) Provisional application No. 60/447,757, filed on Feb. 14, 2003.

(51) Int. Cl.
*C07C 43/11* (2006.01)

(52) U.S. Cl.
USPC ........... 568/622; 568/618; 568/619; 568/696; 568/679

(58) Field of Classification Search
None
See application file for complete search history.

(56) References Cited

PUBLICATIONS

Chen et al. JOC, 1999, 64, 6870-6873.*

* cited by examiner

*Primary Examiner* — Yevegeny Valenrod
(74) *Attorney, Agent, or Firm* — Mueller Law, LLC; Jerry K. Mueller, Jr.

(57) ABSTRACT

Aspects of the present invention are directed to novel methods for making discrete polyethylene compounds selectively and specifically to a predetermined number of ethylene oxide units. Methods which can be used to build up larger dPEG compounds (a) containing a wider range of utility to make useful homo- and heterofunctional and branched species, and (b) under reaction configurations and conditions that are milder, more efficient, more diverse in terms of incorporating useful functionality, more controllable, and more versatile then any conventional method reported in the art to date. In addition, the embodiments of the invention allow for processes that allow for significantly improving the ability to purify the intermediates or final product mixtures, making these methods useful for commercial manufacturing dPEGs. Protecting groups and functional groups can be designed to make purification at large scale a practical reality. The novel dPEG products form the compositional and material basis for making other novel compounds of valuable application in the fields of diagnostics and therapeutics, amongst others.

79 Claims, No Drawings

SELECTIVE AND SPECIFIC PREPARATION OF DISCRETE PEG COMPOUNDS

CROSS REFERENCE TO RELATED APPLICATIONS

This application is a divisional application of U.S. Ser. No. 11/203,950, filed Aug. 15, 2005, and claims priority on international application no. PCT/US2004/004274 filed on Feb. 13, 2004; which claims priority on provisional application Ser. No. 60/447,757, filed Feb. 14, 2003, the disclosure of which is expressly incorporated herein by reference.

STATEMENT REGARDING FEDERALLY SPONSORED RESEARCH

Not applicable.

BACKGROUND OF THE INVENTION

Polyethylene glycols are a family of polymers produced from the condensation of ethylene glycol, usually initiated with base, and have the general formula, HO—$(CH_2CH_2O)_n$—H, where n, the number of ethylene glycol groups, is greater than or equal to 4. Generally, the designation of a polyethylene glycol (PEG) includes a number that corresponds to its average molecular weight, $M_n$, which indicates the extent of polydispersity. All commercial PEG's are polydisperse. For example, polyethylene glycol 1500 refers to a mixture of polyethylene glycols having an average value n of between 19 and 48 (with some even smaller and some larger) and a molecular weight range from about 800 to 2100 grams/mole.

The properties of polyethylene glycols vary with the polymer's molecular weight. Polyethylene glycols have been used in plasticizers, softeners and humectants, ointments, polishes, paper coatings, mold lubricants, bases for cosmetics and pharmaceuticals, solvents, binders, metal and rubber processing, permissible additives to foods and animal feed, and laboratory reagents, among others. Polyethylene glycols generally are linear or branched. PEGs are neutral polyether molecules that are soluble in water and organic solvents. In addition to the uses noted above, polyethylene glycols have proven valuable in many biotechnical and biomedical applications. Polyethylene glycols have been advantageously employed in these applications for their ability to impart water solubilization and surface protective properties, and also because these polymers are only weakly immunogenic.

Polyethylene glycols also have been covalently coupled to proteins to alter their properties in ways that extend their potential uses. Due to in vivo instability, the efficacy of a number of therapeutic proteins is severely limited. While many approaches to stabilization of such proteins have been made, the covalent modification of proteins with hydrophilic polymers, such as dextran and polyethylene glycols, has been most successful. Typically, polyethylene glycol-protein conjugates are more stable than the native protein in vivo and often, the modified proteins exhibit enhanced resistance to proteolytic degradation. The result is an increase in the therapeutic proteins' life in circulation and a reduction in its immunogenicity. In some instances, the therapeutic efficacy of these conjugates is greatly enhanced compared to the native protein.

The improved performance of PEG-modified conjugates has resulted in their development as therapeutic agents. Examples of polyethylene glycol-modified proteins include PEG-adenosine deaminase (PEG-ADA), which has been used in enzyme replacement therapy for immunodeficiency due to ADA deficiency (M. S. Hershfield, *Clin. Immunol. Immuno. Pathol.*, Vol. 76, S 228-232, 1995); PEG-recombinant human granulocyte colony stimulating factor (PEG-rhG-CSF), which showed an increase in stability and retention of in vivo bioactivity and has been suggested as a suitable form of the protein for inclusion in an oral delivery formulation (P. K. E. Jensen et al., *Pharm. Res.*, Vol. 13, pp. 102-107, 1996); PEG-natural human tumor necrosis factor alpha, which showed a gradual decrease in specific activity with increasing degree of PEG-modification and a drastic increase in plasma half-life upon PEG-modification (Y. Tsutsumi et al., *Br. J. Cancer*, Volume 71, pp. 963-968, 1995); PEG-recombinant human interleukin-2, which retains the in vitro and in vivo activity of interleukin-2, but exhibits a markedly prolonged circulating half-life (T. Menzel et al., *Cancer Bio. Ther.*, Vol. 8, pp. 199-212, 1993); and PEG-asparaginase, which has shown promise in patients suffering from acute lymphocytic leukemia (N. Burnham, *Am. J. Hosp. Pharm.*, Vol. 52, pp. 210-218, 1994). Polyethylene glycol conjugates of oligonucleotides also have been prepared and show a more than tenfold increase in exonuclease stability (A. Jaschke et al., *Nucleic Acids Research*, Vol. 22, pp. 4810-4817, 1994).

Other PEG-modified proteins include, inter alia, papain (C. Woghiren et al., *Bioconjugate Chemistry*, Vol. 4, pp. 314-318, 1993), asialofetuin (L. Roseng et al., *J. Biol. Chem.*, Vol. 267, pp. 22987-22993, 1992), collagen (C. J. Doillon et al., *Biomaterial Sciences Polymers*, Vol. 6, pp. 715-728, 1994), RGDT peptides (I. Saiki, *Japanese J. Cancer Research*, Vol. 84, pp. 558-565, 1993), serum IgG (R. Cunningham et al., *J. Immunol. Methods*, Vol. 152, pp. 177-190, 1992), alpha 1-proteinase inhibitor (A. Mast et al., *J. Lab. Clin. Med.*, Vol. 116, pp. 58-65, 1990), growth hormone releasing factor (A. Felix, *Int. J. Peptide Protein Research*, Vol. 46, pp. 253-264, 1995), basic fibroblast growth factor (S. Kusstatscher et al., *J. Pharmacol. Exp. Ther.*, Vol. 275, pp. 456-61, 1995), and catalase, uricase, honey bee venom, hemoglobin, and ragweed pollen extract. As indicated by the number of utilities noted above, polyethylene glycol has recently been widely used to develop new therapeutic agents. Two of the best general references to these applications are the monographs edited by J. Milton Harris:

(a) *Poly(ethylene glycol) Chemistry: Biotechnical and Biomedical Applications*, J. Milton Harris, ed., Plenum Press, New York, 1992.

(b) *Poly(ethylene glycol): Chemistry and Biological Applications*, ACS Symposium Series, Vol. 680, J. Milton Harris and Samuel Zalipsky, eds., American Chemical Society, Washington, D.C., 1997.

Despite the widespread use of polyethylene glycols to modify therapeutic agents, their use has not been without associated disadvantages. The covalent attachment of polyethylene glycol to superoxide dismutase produces a heterogeneous mixture of modified protein species. The heterogeneity of the product derives from, in part the polydispersity of the polyethylene glycol reagent (J. Snyder, et al., *J Chromatography*, Vol. 599, pp. 141-155, 1992.)

These associated disadvantages are due solely to the polydisperse and multicomponent nature of the polymeric polyethylene glycols which are currently being used exclusively, as no discrete alternatives are available. Even the polydispersed products available and being applied are limited to molecular weights above about 2000 (average n greater than about 40-50) due to the higher Mn and molecular weight distributions of the lower MW's, among others. Comments in a recent article, "Synthesis of Polyamide Oligomers Based on 14-Amino-3,6,9,12-tetraoxatetradecanoic Acid," S. M.

Ansell, et al., *Bioconjugate Chem.*, 11, 14-21 (2000), are indicative of the extent of the real problems, as well as pointing directly to the value and importance of the dPEG's.

Fine-tuning the behavior of these systems presents considerable challenges, in part due to the nature of the PEGs that are commercially available. Systems being developing for drug delivery are based on liposomes or lipid-based particulates for the delivery of conventional therapeutic agents or genetic medicines. Problems include a limited selection of molecular weights for both monofunctional and heterobifunctional derivatives, polydispersity variablility, and average molecular weight variability of these compounds, which potentially leads to reproducibility issues with different batches and varible exchange rates associates with different size populations. In addition, the presence of low molecular weight homomers in PEG would result in a small population of PEG-lipid, which would not be rapidly exchanged out of formulations in vivo and potentially could have major implications in systems where immune responses against PEG are an issue.

Commercially available polyethylene glycols having molecular weights greater than about 250 grams/mole are available only as mixtures of varying length polymers. The range of PEG polymer lengths results form the polymerization process by which the PEG polymers are prepared. Commercially available PEG polymers include polymers, inter alia, having average molecular weights of 200, 300, 400, 600, 900, 1000, 1500, 2000, 3400, 4000, 4600, 8000, 10000, 20000, 35000, 200000, 300000, 400000, 600000, 900000, 1000000, 2000000, 4000000, 5000000, 7000000, 8000000, etc. The exact composition of these mixtures is never provided and is of generally a broad range of MW range. However, where terminal monomethyl ethers are desired, these MW ranges are considered to be less broad or narrower then the bis-hydroxyl. This is consistent with the way they are polymerized and initiated with the methoxide, therefore growing randomly from only one end versus growing at both ends of the polymer. Statistically the methoxy terminated would have a narrower range of MWs. However, due to the presence of water in these initiations, there is as much as 25% of the polydiol present, resulting in an even broader MW range.

Accordingly, there remains a need in the art for alternatives to PEG polymers composed of a mixture of lengths and molecular weights to overcome the difficulties associated with the preparation, process variability and/or reproducibility, purification, characterization, and therapeutic administration of such PEG mixtures. The present invention seeks to fulfill these needs and provides further related advantages.

A number of methods have been tried in literature using a more conventional organic synthetic approach to making discrete polyethylene glycol oligomers. Booth and co-workers tried using a convergent-like approach. They did not place protecting groups on the ends of the diols and obtained complex mixtures of oligomers. These could only be separated using complicated and time consuming methods in very low yields. The reaction times also were very long (Refs.: A. Marshall, R. H. Mobbs and C. Booth, "Preparation of Ethylene Glycol Oligomers," *European Polymer Journal*, Vol. 16, pp. 881 to 885, 1980; H. H. Teo, R. H. Mobbs and C. Booth, "Preparation of Ethylene Glycol Oligomers-II," *European Polymer Journal*, Vol. 18, pp. 541 to 544, 1982; S. G. Yeates, H. H. Teo, R. H. Mobbs and C. Booth, "Ethylene Glycol Oligomers," Makromol. Chem., Vol. 185, pp. 1559 to 1563, 1984).

Harris demonstrated a solid phase synthetic approach to making monodispersed oligomers. (Ref. J. Milton Harris, et al., *Poly(ethylene glycol) Chemistry: Biotechnical and Biomedical Applications*, J. Milton Harris, ed., Plenum Press, New York, 1992, pp. 371-381). However, this is not a practical approach for scale-up and he found that due to the nature of using a polymer support, the steps are very slow and require high temperatures to complete. And as is the case with polymer support reactions, the valuable building blocks have to be used in considerable excess to achieve complete reactions. Dr. Harris also mentions that their attempts at solution phase synthesis "have proven to produce low yields of products that are difficult to purify."

Svendhem, et al., have made a series of monodispersed amino-PEG-alcohols using ether coupling chemistry similar to the stepwise approach, but they found that "the couplings were sluggish and slow, and purification by HPLC was necessary to obtain pure compounds (on mg scales). Efforts to optimize the yields by changing solvent and bases, or phase-transfer conditions were all unsuccessful." (Ref. S. Svedhem, C.-A. Hollander, J. Shi, P. Konradsson, B. Liedberg, and S. C. T. Svensson, "Synthesis of a Series of Oligo(ethylene glycol)-Terminated Alkanethiol Amides Designed to Address Structure and Stability of Biosensing Interfaces," *J. Org. Chem.*, 66, 4494-4503 (2001)).

More recently Chen and Baker have demonstrated a very limited example of the convergent synthesis of monodispersed PEGs. However, the conditions for the only protecting group are extremely severe, the reaction times long, and they show only examples using small commercially available diols. (Ref. "Synthesis and Properties of ABA Amphiphiles," Yiyan Chen and Gregory L. Baker, *J. Org. Chem.*, 64, 6870-6873 (1999).

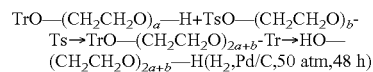

In addition to the other limitations, each of these methods relies on having a preformed or pregenerated alkoxide species, which is very basic and nucleophilic, and has the potential of leading to varying amounts of undesirable by-products, either via side reactions of with secondary reactions on the desired product. A preferred embodiment of the current invention significantly reduces and maybe eliminate this potential by generating the reactive species in situ.

More recently in published application US 2003/0004304 A1 (Ekwuribe, et al., "Methods of Synthesizing Substantially Monodispersed Mixtures of Polymers having Polyethyene Glycol Moieties," publication date, Jan. 2, 2003), the inventors propose a stepwise-like approach to make "substantially mondispersed mixture of polymers." This patent application proposes a process for making "substantially monodispersed mixtures of polymers" using a process directed to their interests in synthesizing the smaller versions of their "substantially monodispersed mixtures of polymers" attached to highly lipophilic substituents. Ekwuribe still speaks in terms of "mixtures" of polymers, rather than discrete species, as in the present invention. Processing details also are quite different. Production of discrete PEGs with a predetermined number of ethylene oxide units is not possible. Moreover, Applicants' stepwise synthesis scheme is totally absent from Ekwuribe.

BRIEF SUMMARY OF THE INVENTION

Aspects of the present invention are directed to novel methods for making discrete polyethylene compounds selectively and specifically to a predetermined number of ethylene oxide units. Methods which can be used to build up larger dPEG compounds (a) containing a wider range of utility to make useful homo- and heterofunctional and branched species, and (b) under reaction configurations and conditions that are milder, more efficient, more diverse in terms of incorporating useful functionality, more controllable, and more versatile then any conventional method reported in the art to date. In addition, the embodiments of the invention allow for processes that allow for significantly improving the ability to purify the intermediates or final product mixtures, making these methods useful for commercial manufacturing dPEGs. Protecting groups and functional groups can be designed to make purification at large scale a practical reality. The novel dPEG products form the compositional and material basis for making other novel compounds of valuable application in the fields of diagnostics and therapeutics, amongst others.

A. Convergent Approach to Synthesize dPEGs

One embodiment of the invention is described as a "convergent" method for selectively building up larger discrete homologues of dPEGs very rapidly and efficiently from readily, cheaply, and commercially available starting materials, such as, but not limited to tetraethylene glycol. A preferred embodiment of the convergent method for selectively making dPEG homologues incorporates the following general reaction scheme:

A dPEG compound having a general structural formula XXII $$R^1\text{-}dPEG_x\text{-}OH \qquad \qquad XXII$$

is mixed together with a dPEG compound having the structural formula II;

$$R^2\text{-}dPEG_y\text{-}OR^2 \qquad \qquad II$$

in the presence or absence of a catalyst, wherein $R^1$ is a hydroxyl protecting group (PG) or a functional group (FG); x is 1 to 100, $R^2$ is a leaving group, y is from 1 to 100.

Compounds XXII and II ("compound" is used as a shorthand for "compound of structural formula" often in the description that follows for brevity) are caused to react to produce compound III under conditions when a compound capable of ionizing compound XXII to compound I (see below) is added to the mixture of compounds XXII and II.

$$R^1\text{-}dPEG_{2x+y}\text{-}R^1 \qquad \qquad III$$

This embodiment in particular allows for a much more efficient and mild means of convergently building up a mixture of specific dPEG compounds than has been available before. In this case in particular, the use of an agent to ionize the hydroxyl functional group of the compound of structural formula XXII and the rapidity of the resulting ionic species to react with compound II in the presence or the absence of a complexing catalyst, allows one to carry out the method very much like a titration for making compounds III.

A further embodiment of the convergent approach incorporates a method where the compound of structural formula I is pre-generated with an ionizing compound and includes the following general reaction scheme of reacting a dPEG compound (or discrete ethylene oxide homologue) having the structural formula I $$R^1\text{-}dPEG_x\text{-}O^-M^+ \qquad \qquad I$$

in the presence of a catalyst, with a dPEG compound (discrete ethylene oxide homologue) having the structural formula II $$R^2\text{-}dPEG_y\text{-}OR^2 \qquad \qquad II$$

under conditions to produce a dPEG compound (a discrete ethylene oxide homologue) having the structural formula III $$R^1\text{-}dPEG_{2x+y}\text{-}R^1 \qquad \qquad III$$

wherein $R^1$ is a hydroxyl protecting group (PG) or a functional group (FG), x is 1 to 100, $M^+$ is a positively charged moiety, $R^2$ is a leaving group, and y is from 1 to 100.

When the protecting group is selected properly, compound III is deprotected and becomes the starting material, e.g., like compound IV and like compounds derived from compound VI, for making larger dPEGs, using the same convergent process or incorporating them into the stepwise embodiment of the invention described below.

Methods for making compounds XXII, II, X, and XI (see below) and their homologues are described further below in the detailed embodiment of the invention.

B. Stepwise Approach to Heterobifunctional dPEGs

The present embodiment uses the same methods for selectively and rapidly producing dPEG compounds, except the goal is to produce directly final product that can selective built up or directly converted to useful heterobifunctional dPEG compounds. This embodiment incorporates the following:

A dPEG compound having structural formula XXII $$R^1\text{-}dPEG_x\text{-}OH \qquad \qquad XXII$$

wherein $R^1$ is a hydroxyl protecting group (PG) or a functional group (FG); x is 1 to 300, is mixed with a dPEG compound (discrete ethylene oxide homologue) having the structural formula X; in the presence or absence of a catalyst;

$$R^3\text{-}dPEG_y\text{-}OR^2 \qquad \qquad X$$

wherein $R^2$ is a leaving group, y is from 1 to 300, $R^3$ is a hydroxyl protecting group or functional group Then compounds of structural formulas XXII and X are caused to react to produce selectively a compound of structural formula XI when a compound that is capable of ionizing compound of structural formula XXII to compound of structural formula I is added to the mixture of compounds of structural formulas XXII and X.

$$R^1\text{-}dPEG_{x+y}\text{-}R^2 \qquad \qquad XI$$

A further embodiment of the stepwise approach incorporates a method where the compound of structural formula I is pre-generated with an ionizing compound and includes:

Reacting a dPEG compound having the structure of formula I $$R^1\text{-}dPEG_x\text{-}O^-M^+ \qquad \qquad I$$

Where, $R^1$ is a hydroxy protecting group (PG) or a functional group (FG); x is 1 to 300; $M^+$ is a positively charged moiety, in the presence of a catalyst, with a dPEG compound having the structural formula X $$R^3\text{-}dPEG_y\text{-}OR^2 \qquad \qquad X$$

Where, $R^2$ is a leaving group, $R^3$ is a hydroxyl protecting group or functional group; y is from 1 to 300, under conditions to provide a dPEG having the structural formula XI $$R^1\text{-}dPEG_{x+y}\text{-}R^3 \qquad \qquad XI$$

In order to produce the preferred range of heterobifunctional compounds or precursors for the same, there are several criteria placed on the nature and identity of $R^1$ and $R^3$. Where $R^1$ and $R^3$ are both hydroxy protecting groups, they must be different and able to be selectively removed in the presence of the other. When $R^1$ is a protecting group and $R^3$ a functional group and vice versa, they are chosen so that the one is stable in the presence of the other while it is undergoing removal or further transformations. The options to meet many of these criteria are well known in the art and can be applied.

For example, when $R^1$ or $R^3$ are hydroxyl protecting groups, and $R^1$ is selectively removed in the presence of $R^3$ and vice versa, compounds of formulas XII and XIII are produced, respectively. The same compounds would be produced if $R^1$ or $R^3$ is a functional group, respectively.

$$HO\text{-}dPEG_{x+y}\text{-}R^3 \quad\quad\quad XII$$

$$R^1\text{-}dPEG_{x+y}\text{-}OH \quad\quad\quad XIII$$

The compounds of structural formulas XII and XIII can either be converted to compounds like structural formula II where the hydroxy group is converted to a leaving group and the dPEG is built up further by reaction with a structure like formulas I or XXII in the presence of an ionizing reagent. The hydroxyl group can be transformed into a variety of functional groups like the amine, carboxyl, thiol and others, by methods well known in the art of organic chemistry.

C. Synthesis of Branched dPEGs

This embodiment employs a method for selectively making specific discrete polyethylene glycol (dPEG) compounds containing a discrete and predetermined number of ethylene oxide moieties, which are incorporated into branching systems. This embodiment incorporates the steps of reacting a first reactant having the general structural formula XXII:

$$R^3\text{—}X\text{—}(OH)_p \quad\quad\quad XXII$$

with a second dPEG compound having the general structural formula II $$R^4\text{-}dPEG_y\text{-}OR^2 \quad\quad\quad II$$

in the presence of an ionizing compound capable of ionizing dPEG compound XXII reactant and under reaction conditions to produce a dPEG compound having the general structural formula III $$R^3\text{—}X\text{—}(O\text{-}dPEG_yR^4)_p \quad\quad\quad III$$

wherein dPEG represents a discrete ($OCH_2CH_2$) moiety, each $R^3$ independently is a functional group (FG) or protecting group (PG); y ranges from about 1 to 100, $R^2$ is a leaving group, $R^4$ is a functional group or protecting group and is different than $R^3$, y ranges from about 1 to 100; X is an organic moiety which is alkyl, aryl or aralkyl with one or more substituents and may contain the hydroxy functionality; p ranges from 2 to about 4.

One also can react $R^3$—X—$(R^2)_q$ with $R^4$-$dPEG_y$-OH in the presence of an ionizing agent to make compound III.

Higher branching systems can be formed from compound III. For example, $R^3$ in compound III can be converted to (if a functional group) or deprotected (if a protecting group) to compound XXIV and reacted with $R^3$—X—$(R^2)_q$ as shown below.

$$R^3\text{—}X\text{—}(O\text{-}dPEG_yR^4)_p(XXIV)+R^3\text{—}X\text{—}(R^2)_q \rightarrow R^3\text{—}X\text{—}(\text{—}(O\text{-}dPEG_yR^4)_p)_q$$

This can be continued to produce even higher branched systems.

The various building blocks for these branching dPEG systems can come from either the convergent, stepwise, or a combination of those two embodiments of this invention.

Compound III additionally can be converted to as follows:

$$R^3\text{—}X\text{—}(O\text{-}dPEG_yR^4)_p \rightarrow \rightarrow R^3\text{-}dPEG_x\text{-}X\text{—}(O\text{-}dPEG_yR^4)_p \quad\quad\quad (XXV)$$

DEFINITIONS

In order to fully understand the present invention, the following definitions are provided.

(a) "Discrete PEG" or "dPEG" (used interchangeably), as used herein, is an important aspect of this invention and refers to an poly(ethylene oxide) organic composition of a single molecular entity (versus a mixture which contains two or more molecular entities). Whether one is manufacturing a chemical intermediate or a therapeutic, the goal is to obtain a single product of interest, rather than a mixture of the product of interest and by-products. The processes and methods described in this invention for manufacturing dPEGs and their derivatives are specific to a single or discrete ethylene oxide homolog. A specific product (dPEG) is produced and isolated, not a complex polydisperse mixture, as in all polymer processes, like those used to make commercial PEGs.

In the present context dPEG is used to clarify the discrete nature of the composition, where $dPEG_x$ and its x subscript are used to represent the specific number of ethylene oxide subunits in the specific compound obtained. The actual discrete number of ethylene oxide units is indicated by the subscript on the ethylene oxide subunit, —$CH_2CH_2O$—, which is abbreviated as $dPEG_x$, X=one specific integer from 1 or 2 or 3 or 4 or an integer up to at least 100, or as the drawn chemical structure is indicated as (—$CH_2CH_2O$—)$_x$. An example of the $dPEG_7$ is shown below, namely heptaethylene glycol, HO—($CH_2CH_2O$—)$_7$—H, where n=7.

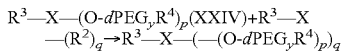

Heptaethylene glycol
$C_{14}H_{30}O_8$
Mol. wT.: 326.38

Polymeric compositions typical of all commercially available PEGs are complex polydisperse mixtures. Polymeric compositions are polydisperse due to the random and chain-growing processes used to build polymers. This invention does not use these or like processes, but rather a unique stepwise organic process, involving standard organic techniques and methodology known to organic chemists skilled in the art. The science of polymer chemistry is largely directed towards understanding and controlling the numerous variables that determine the extent or breadth of polydispersity in the final product. All commercial PEG formulations are polydisperse, generally arising from anionicaly initiated and propagated processing.

Most of the science and application of polymer chemistry is focused in the area of understanding and "controlling" the tremendous range of variables that effect the molecular weight distribution and, therefore, the polydispersity of the resultant polymers. This applies even to the simplest formulations and the best chemistries found to date to narrow this product distribution. The nature of polymer processes will never result in the making of a single pure component. The idea of a monodisperse polymer is primarily theoretical in nature. Reference is made to an introductory text in polymer chemistry such as, inter alia, Dr. George Odian's, *Principles of Polymerization*, (ISBN 0-471-05146-2), to fully appreciate the complexity of the science of controlling the molecular weight distributions of polymers.

Most polymers are analyzed to determine their PDI, which represents their polydispersity index or the molecular weight distribution of the polymer sample. The common thermal- and photo-initiated acrylate polymerizations give PDXXIIs at least >1.5, often as high as 20-50 (the higher the number the broader the distribution and the more different compounds in the sample). An idealized example cited in Odian's book (pg. 389) of an extremely narrow distribution has a PDI=1.002. For a polymer with an average MW of 500,000 having a Poison distribution and a PDI=1.002, 95% of the individual polymer products have MW's between 450,000 and 550,000. If the monomer were styrene, with a MW of about 100, this would represent a mixture of at least 1,000 different compounds. Actual polymerizations of this living anionic polymerization example for making MW "standards" have PDXXIIs of 1.06-1.12.

(b) The term "discrete", as used herein, means a single molecular entity and not a mixture of molecular entities (such as those resulting from a random polymerization reaction or a random labeling reaction). The discreteness of the inventive dPEGs (i.e., discrete PEG's) compounds distinguishes them from the polydisperse art.

Throughout this invention, the acronym PEG is used to refer to the polydisperse and complex mixture of compounds present in commercial preparations of polyethylene glycol).

(c) Protecting group (PG), as used herein, means a molecular group that blocks a functional group from reacting during other chemical operations/transformations. A PG is inert to these chemical operations/transformations. After the chemical transformations are complete, the PG can be removed or cleaved by specific chemical means such that it liberates the original functional group for further reaction. The chemical selectivity and the physical design of protecting groups are important to this invention. There are a wide variety of protecting groups available and known in the art. Many of them can be used in the present invention. On the other hand, preferred structural and physical properties can be built into the protecting group for enhancing the process for making and purifying/isolating our dPEG molecules as taught in this invention. The most often and important protecting groups used in this invention are the ones used to protect the hydroxyl group, as well as the amino and sulfhydryl functional groups. In this invention, 2,4,6-trimethylbenzyl group (TMB) is a preferred hydroxyl protecting group, because it facilitates the purification and gives improved selectivity when reacted with glycols. For example, when tetraethylene glycol is reacted with 2,4,6-trimethylbenzyl chloride in the presence of base, the mono-protected TMBO-dPEG$_4$-OH is obtain almost exclusively in preference to the bis-product (TMBO-dPEG$_4$-OTMB) when excess glycol is used. Any hydroxyl protecting groups in the art can be used if stable to the reaction conditions. Other preferred protecting groups can be selectively removed in the presence of other protected alcohols or other protected functionality. For example, the THP (tetrahydropyan-2-yl) can be removed with acid in the presence of the benzyl. Also, the PMB (p-methoxybenzyl) and DMB (3,4-dimethoxybenzyl) protecting groups can be removed in the presence of the THP and/or benzyl, but also can be deprotected with reduction like the benzyl. There are many other strategies for the selective use of protecting groups known in the art, which can be applied to this invention. The PMB and DMB type protecting group is useful since a range of groups, other than the methyl group, can be substituted on the base p-cresol and 4-methylcatecol to control and modify the polarity and solubility's of the corresponding substituted dPEG$_x$ intermediates.

However, the dPEG backbone can be extended with the termini functionality being a protected amine, e.g., using CBZ—NH-dPEG$_x$-OH, (including as the azide, as well), thiols, carboxylic acids, and any others known in the art and can be protected with stability under the conditions of process for making dPEG's. For example, N$_3$-dPEG$_{12}$-OTMB can be elongated further after cleavage of the TMB group with anhydrous TFA in CH$_2$Cl$_2$ to give azido alcohol, N$_3$-dPEG$_8$-OH. The latter can be tosylated, N$_3$-dPEG$_{12}$-OTs, and then reacted with an alkoxide, TMBO-dPEG$_8$-ONa, to give the TMBO-dPEG$_{20}$-N$_3$. This reaction sequence can be repeated indefinitely to give higher and higher homologues. See the reaction scheme below.

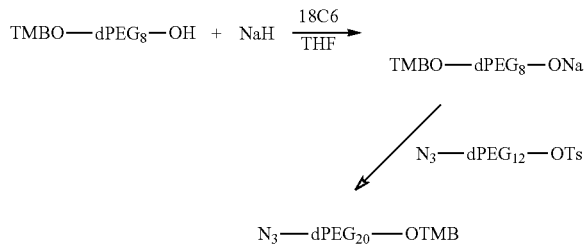

The above is an example of elongation of a dPEG entity in a discrete manner. The above product is the precursor to the following types of compounds as listed below and above.

Cbz-NH-dPEG$_{12}$-OTMB   H$_2$N-dPEG$_{12}$-OCH$_2$CH$_2$CO$_2$4-bu

Cbz-NH-dPEG$_{12}$-OH H$_2$N-dPEG$_{12}$-OH

Cbz-NH-dPEG$_{12}$-OCH$_2$CH$_2$CO$_2$-t-bu   H$_2$N-dPEG$_{12}$-OCH$_2$CH$_2$CO$_2$H

The amino alcohol comes from the reducing the Cbz group of Cbz-NH-dPEG$_{12}$-OH in the presence of Pd/C and H$_2$ or triphenylphosphine. The H$_2$N-dPEG$_{12}$-OH produced is converted to boc-NH-dPEG$_{12}$-OH, which in turn is converted to boc-NH-dPEG$_{12}$-OCH$_2$CH$_2$CO$_2$-t-bu. The ester function is converted into the carboxylic acid via saponification and neutralization with an equivalent of acid under anhydrous conditions at 0° C. to give boc-NH-dPEG$_{12}$-OCH$_2$CH$_2$CO$_2$H. This same product also can be made by making the N$_3$-dPEG$_{12}$-OCH$_2$CH$_2$CO$_2$H, then reducing with Pd/C and H$_2$ in presence of the di-t-butyl dicarbonate, as follows:

Reaction:

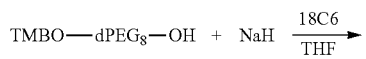

-continued

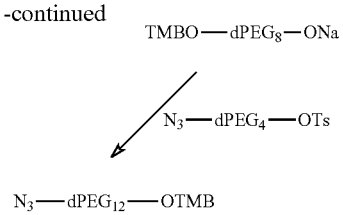

The protecting group will vary depending on the type of chemically reactive group being protected. For example, if the chemically reactive group is a hydroxyl group, the protecting group can be selected from a large group, such as 2,4,6-trimethylbenzyl and benzyl derivatives, trialkylsilyl, alkylarylsilyl, THP (tetrahydropyran-2-yl), PMB, DMB and trityl derivatives. If the chemically reactive group is an amine or a hydrazide, the protecting group can be selected from the group of tert-butyloxycarbonyl (t-boc), benzyloxycarbonyl (N-Cbz or Z), 9-fluorenylmethoxycarbonyl (Fmoc), and benzyl. If the chemically reactive group is a thiol, the protecting group can be othopyridyldisulfide, thiourea, trityl, or acetyl. If the chemically reactive group is a carboxylic acid, such as acetic, proprionic or butanoic acids, the protecting group can be benzyl, methyl, ethyl, t-butyl. Other protecting groups known in the art for these and other functional groups also may be used in the invention. Many of the applications of protecting groups used in this invention will be apparent to anyone familiar with the art with the exceptions noted for this invention.

References (and references therein) containing extensive descriptions of protecting groups typical of the art, including methods/conditions for their formation and cleavage: (a) Kocienski, Philip J., *Protecting Groups; Thieme Foundation of Organic Chemistry Series*/ed. By D. Enders, R. Noyori, B. M. Trost-Stuggart; New York: Thieme, 1994 and references therein; (b) Theodora W. Green and Peter G. M. Wuts, *Protective Groups in Organic Synthesis*, $2^{nd}$ ed., Wiley-Interscience, New York, 1991 and references therein.

(d) "Leaving group" (LG), as used herein, means a chemical moiety that can be or is displaced by a nucleophile to form a new chemical bond, generally via an $S_N2$ type displacement mechanism. For the present invention, the formed bond of greatest importance is the ether bond (C—O), for building dPEGs with only ethylene oxide or alkyl oxide units as the basic chemical backbone, though other bond forming reactions can be utilized to form dPEGs containing other linkages, including, for example, C—N, C—C, C—S. Other bonds also are formed where the terminus, termini, or internal portions of the dPEG will be to useful functional groups, which can be used to incorporate the $dPEG_x$ unit into a variety of applications. The preferred leaving group in this invention is the p-toluenesulfonate or Ts group. However, others known in the art, like the Ms (methanesulfonate), also are useful.

Thus, leaving group is a term well known in the art and usually used without definition. Reference leaving groups: (a) Thomas H. Lowry and Kathleen Schueller Richardson, *Mechanism and Theory in Organic Chemistry*, Harper& Row, New York, 1976, p. 192; (b) Jerry March, *Advanced Organic Chemistry: Reactions, Mechanisms, and Structure*, $4^{th}$ Ed., John Wiley and Sons, New York, 1992, pp. 352-357.

(e) "Homogenous dPEG", as used herein, means a discrete PEG structure whose entire chemical backbone is made up of a continuous and specific number of only ethylene oxide units. In other words, no other functionality is present within $dPEG_x$, e.g., amide or other linkages. The termini of the homogeneous dPEG, however, can be any combination of functional groups, from the pure homogeneous dPEG with hydroxyl, OH, as the terminal and only functional groups, to any other combination, either homo- or heterobifunctional, of functional groups known in the art of organic chemistry. See definition of "functional group" (FG) below for examples. These homogeneous dPEG's can then become and included as parts or portions of a more complex structure, e.g., a branched dPEG from a multifunctional core structure.

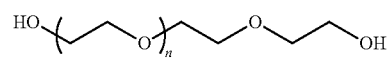

Homogeneous dPEG with terminal OH functional groups n=1 . . . 100

(f) "Heterogeneous dPEG", as used herein means a discrete PEG structure where the basic ethylene oxide backbone of a continuous, specific, and known number of ethylene oxide units is intact, but where it can be broken or substituted by the presence of other functional groups or units, such as, e.g., inclusion of the amide or ester bonds, the thioether, a urea bond, a trimethylene or higher alkane unit, amine, 2° or 3° and other functional units that are useful and usable for building a variety of versatile and complex structures incorporating the valuable properties of the dPEGs of the present invention.

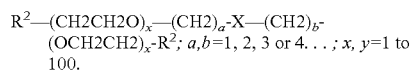

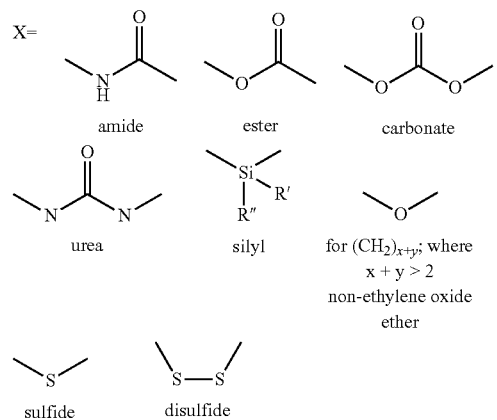

(g) "Oligomers", as used herein, means oligomers are polymer chains of any length and such term is used interchangeably with the term polymer. Oligomers, however, do not to refer to the discrete PEG systems, which are the subject of this invention. Admittedly, the term, "oligomer", is used very loosely in the art, often to define a "smaller" polymer or "shorter" polymer chains, e.g., when specifically defined the number of subunits is from 2-5; but, when used in practice, like some of the prior art discussed below, has been applied to much larger species.

(h) The terms "functional group" (FG), "active moiety," "activating group," "reactive site," "chemically reactive group," and "chemically reactive moiety", as used herein, refer to distinct, definable portions or units of a molecule and can be used interchangeably (substiuents A and B from Table 2 and related description associated therewith). The terms are somewhat synonymous in the chemical arts and are used herein to indicate the portions of the molecules that perform some function or activity and are reactive or reactable with other molecules. The term "active," then, when used in conjunction with functional groups, is intended to include those functional groups that react readily with electrophilic or nucleophilic groups on other molecules, in contrast to those groups that require strong catalysts or highly impractical reaction conditions in order to react. For example, as would be undertaken in the art, the term "active ester" would include those esters that react readily with nucleophilic groups such as amines. Typically, an active ester will react with an amine in aqueous or organic media in a matter of minutes at ambient temperatures, whereas certain esters, such as methyl or ethyl, require a moderately strong catalyst like bicarbonate in order to react with a nucleophile or to generate the reactive nucleophile. Useful "functional" groups in this invention include, but are not limited to the following: hydroxy, protected hydroxyl, active ester, such as N-hydroxysuccinimidyl ester and 1-benzotriazolyly esters, active carbonate, such as N-hydroxysuccinimidyl carbonates and 1-benzotriazolyl carbonates, acetal, aldehyde, aldehyde hydrates, epoxide, alkenyl, acrylate, methacrylate, acrylamide, active sulfone, protected amine, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones. The functional group often is chosen for attachment to a functional group (FG) on a biologically active agent or to build up a more complex and designed dPEG based structure.

(i) "Linkage" or "linker", as used herein, refer to groups or bonds that normally are formed as the result of a chemical reaction and typically are covalent linkages. In the invention, the linker contains the dPEG molecule(s) containing the appropriate functional groups (FG) for a particular application, which allows it to be linked optimally between at least two other molecules of practical interest. The term also can be applied to dPEGs which are incorporated into the branched structures of this invention. The resulting compounds, especially those of biological interest, are known as "conjugates." (Ref.: Greg Hermanson, "*Bioconjugate Technique*", Academic Press, Inc., San Diego, Calif., 1996 (ISBN 0-12-342335-X)). Hydrolytically stable linkages means that the linkages are substantially stable in water and do not react with water at useful pHs, e.g., under physiological conditions for an extended period of time, perhaps even indefinitely. Hydrolytically unstable or degradable linkages mean that the linkages are degradable in water or in aqueous solutions, including for example, blood or other biological fluids. Enzymatically unstable or degradable linkages mean that the linkage can be degraded by one or more enzyme. As understood in the art, dPEG and related molecules may include degradable linkages in the molecular backbone or in the linker group of the molecular backbone and one or more of the terminal functional groups of the linked molecule.

(j) "Biologically active molecule," "biologically active moiety" or "biologically active agent" ("T"), as used herein, means any substance which can affect any physical or biochemical properties of a biological organism or system, including by not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance but are not limited to peptides, proteins, enzymes, small molecule drugs, dyes, lipids, nucleosides, oligonucleotides, cells, viruses, liposomes, microparticles, and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

(k) By convention for ease of understanding and consistency, $R^2$ will be a leaving group in all instances. $R^1$, $R^3$, and other R groups, by convention, either will be a (hydroxy) protecting group or a functional group, and are stable (no reactive) under conditions where $R^2$ is removed. $R^1$, $R^3$, and other R groups may contain oxyethylene moieties or dPEG moieties.

DETAILED DESCRIPTION OF THE INVENTION

According to the preferred embodiments of the present invention, there are three general methods for making discrete PEG (dPEG) compounds. These include:
(a) convergent approach, equation (1);
(b) a stepwise approach, equation (2); and
(c) a method for making branched dPEGs, equations (3).

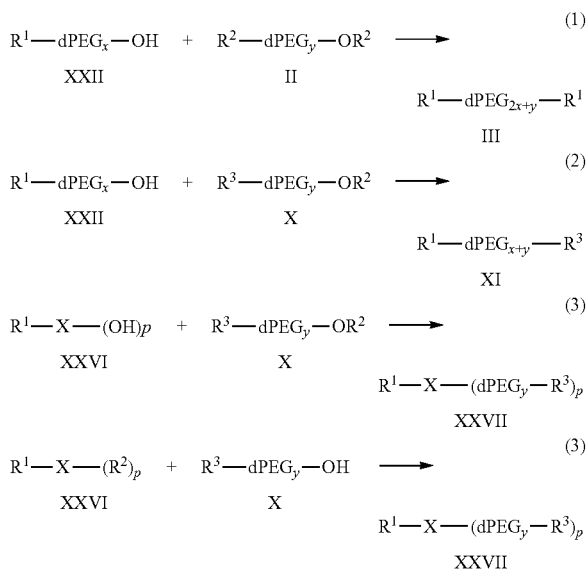

For equations (1), (2) and (3), it is a preferred embodiment that in each case the reactants are combined in a solvent in the preferred stoichiometry, followed by the addition of an ionizing agent for the hydroxyl group, e.g., a solution of potassium t-butoxide. The addition of the ionizing agent cause the dPEG containing the hydroxyl group to act as if the species like compound I is being formed and reacting in situ with the other reactant to form the dPEG products. In effect, this embodiment acts as a titration, where the reaction is titrated to completion with the addition of the ionizing compound. The advantages of this method have already been stated, but include preventing the opportunity for unwanted side reactions of the reactants or the formed dPEG products.

The preferred ionizing agent is potassium t-butoxide. It is very effective due to the rapidity with which it reacts with the dPEG hydroxy and its sterically hindered nature does not readily allow unwanted side reactions. However, other ionizing agents known in the art also can be used, including, but not limited to bases, such as, for example, sodium hydride, t-butyl or n-butyl lithium, and LDA (lithium diisopropylamide).

Another embodiment is the option to preform the dPEG reactant like compound I:

$$R^1\text{-}dPEG_x\text{-}O^-M^+ \qquad \qquad I$$

In this embodiment, compound I is first formed in solution with an ionizing compound like sodium hydride, followed by the addition of the dPEG compound containing the leaving group(s) in solution. The option also exists for a reverse addition embodiment. The preferred values of x and y are from 1 to 1000, with preferred values from 4 to 1000.

$R^2$ is a leaving group from those known in the art. In this invention the tosyl or tosylate (Ts) group is the preferred leaving group. While others may be as effective, the tosylate is a derivative that is very easily made from the alcohol, produce intermediates that are easy to process and purify, and are made from starting materials that are inexpensive and very pure, namely tosyl chloride or p-toluene sulfonyl chloride and triethylamine. Tosyl chloride also is an easy to handle solid. The preferred solvent for making the tosylates is methylene chloride, but others like ethyl acetate may be preferred when these reactions are performed at a process scale of manufacturing.

The reactions can be performed in the presence or the absence of a catalyst. The preferred embodiment uses a catalyst, however in each embodiment, the reactions done when adding the ionizing agent to the mixture, the reaction can be carried out without a catalyst as well for many cases of $R^1$ and $R^3$. The catalyst may provide conditions that are sufficiently mild to present greater range of functional group sensitivity when $R^1$ and $R^3$ is a functional group or a protecting group. The catalyst is chosen from among the many compounds known in the art of metal complexing cryptands that enhance the reactivity of certain ionic species. The preferred catalyst for this invention is the 18-crown-6 (1,4,7,10,13,16-hexaoxachyclooctadecane). Listed below are a number of relevant references to the art in this area.

References:
a. C. J. Pedersen, *J. Am. Chem. Soc.*, 89, 2495, 7017 (1967)
b. C. J. Pedersen, *Angew. Chem., Int. Ed. Engl.*, 11, 16 (1972)
c. J.-M. Lehn, Supramolekulare Chemie., *Angew. Chem.*, Int. Ed. Engl., 27 (1988)
d. J.-M. Lehn, Cryptates: The Chemsitry of macropolycyclic Inclusion Complexes, *Acc. Chem. Res.*, 11, 49 (1978).
e. F. Vogtle and E. Weber (eds.): *Host Guest Complex Chemistry—Macrocycles-synthesis, Structures, Applications*. Springer, Berlin 1985.
f. R. Izatt and J. J. Christensen (eds.): *Synthetic Multidentate Macrocyclis Compounds: Synthesis, Properties, and Uses*. Academic Press, New York, London 1978.
g. G. W. Gokel and H. D. Durst: Principles and Synthetic Applications in Crown Ether chemistry, *Synthesis*, 168 (1976).
h. F. Vogtle and E. Weber: *Progress in Crown Ether Chemistry*, Part IV A . . . IV E. Kontakte (Merck, Darmstadt) 1980 (2), 36ff.; 1881 (1), 24ff.; 1982 (1), 24ff.; 1983 (1), 38ff.; 1984 (1), 26ff.
i. P. Viout: Effects of Macrocyclic Cation Ligands and Quaternary Onium Salts on the Anionic Reactivity. *J. Mol. Catalysis* 10, 231 (1981)
j. D. J. Cram: Cavitands: Organic Hosts with Enforced Cavities. *Science* 219, 1177 (1983)
k. F. De Jong and D. N. Reinhoudt: Stability and Reactivity of Crown Ether Complexes. *Adv. Phys. Org. Chem.* 17, 279 (1980)
l. E. Weber and F. Vogtle: Crown-Type Compounds—And introductory Overives. *Top. Curr. Chem.* 98, 1 (1981)
m. M. Hiraoka: *Crown Compounds. Their Characteristics and Applications*. Elsevier, Amsterdam 1982.
n. C. M. Starks and C. Liotta; *Phase Transfer Catalysis: Principles and Techniques*. Academic Press, New York 1978.
o. E. V. Dehmlow and S. Dehmlow: *Phase Transfer Catalysis*. $2^{nd}$ edition, Verlag Chemie, Weinheim 1983.

The preferred reaction conditions for the reactions include room temperature. The rate of addition of the ionizing agent, preferable a solution of potassium t-butoxide in tetrahydrofuran (THF), is at the rate at which there is no appreciable build up of the ionized species I.

However, to one skilled in the art there are multiple variables that can affect the optimal range of conditions under which the convergent, stepwise, and branched methods can be run. As well as the inherent differences between performing these methods at bench scale versus larger commercial processes. These variables may include the following: (a) the concentrations of the reactants in each method, their reactivity with or without the use of catalyst; (b) the rate of addition and concentration of the ionizing agent; (c) the rate of addition of reactant containing the leaving group, $R^2$, to the preformed alkoxide, compound I; (d) the options of using temperature to favor the formation of the desired dPEG when $R^1$ or $R^3$ is a more sensitive functional group or protecting group versus possible side reactions; (e) the use of different or multiple solvents; and/or (f) the use of different base alternatives with different $R^1$ and $R^3$ combinations. These may be just some examples of the variables that can be used to best optimize the practice of this invention.

The preferred stoichiometries for each embodiment of the convergent, stepwise and branching are:
(a) Convergent: The ideal stoichiometry for the convergent method is 2:1 of compound of formula XXII:compound of formula II. In one embodiment of this invention, where the ionizing agent is added to the mixture of compounds of formula XXII and II, one is able maintain this stoichiometry. If at the end of the initial process there is a slight excess of compound of formula XXII or II, the other compound can be added and more of the ionizing agent titrated into the reaction until only the product of formula III is present. In this case, however, it may be necessary or desirable to have a very slight excess of the compound of formula I be used. The preferred stoichiometry is less that 1.05:1.
(b) Stepwise: The ideal for the stepwise approach is a 1:1 stoichiometry of compound of formula XXII:compound of formula X. Just as above, when the initial process is completed, the stoichiometry of 1:1 can be maintained by adding the compound which is not present in excess, followed by a further and proportionate addition of the ionizing agent to yield only product. As is often the case, it may be impractical to achieve precisely a 1:1 stoichiometry, and the processing advantages inherent in the stepwise approach favor a preference for a stoichiometry of greater than 1:1 of compound of formula XXII to compound of formula X.
(c) Branched dPEGs: In this case again the ideal stoichiometry of the basic embodiment of compound of formula XXVI:compound of formula X is 1:p. Using the method of adding the ionizing agent to a mixture of compounds XXVI and X can approach this ideal. However, since it is vital that all of the p hydroxy groups react completely, it is preferred that a ratio of slightly less than 1:p is maintained, or when a slight excess of compound X is present to ensure complete substitution of compound XXVI. The same is true for the alternative embodiment in equation (3).

Convergent Method Preferred Embodiments

In equation (1), $R^1$ can be a functional group or a protecting group. If $R^1$ is a functional group, the product with the general structural formula III, then the value of 2x+y cannot be increased or the hydroxy groups can be converted into the desired functional groups. However, if $R^1$ is a hydroxyl protecting group, it is removed to give the compound of formula IV

$$HO\text{-}dPEG_{2x+y}\text{-}OH \qquad IV$$

This can be converted to the monoprotected compound, $R^1$-dPEG$_{2x+y}$-OH, with the same or different protecting group or functional group, but one of those preferred to this invention. The hydroxyl groups in IV can also be converted to the ditosylate like compound of the general structural formula V, where $R^2$ is tosyl.

$$R^2\text{-}dPEG_{2x+y}\text{-}OR^2 \qquad V$$

When these are allowed to react with the addition of the ionizing compound, a larger dPEG compound with the general structural formula VI is formed

$$R^1\text{-}dPEG_{4x+2y}\text{-}R^1 \qquad VI$$

This process can be repeated until the value of 4x+2y is up to about 1000. This allows the very rapid production of higher MW dPEG compounds that can be further modified to give homo- or heterobifunctional dPEG compounds. For example, if one starts where x and y are each 4, then after reaction cycles 2x+y is 324, and 5 reaction cycles 2x+y equals 972.

There is a very wide range of options on the choices of the functional and protecting groups.

In the general structural formulas, $R^1$ is either a protecting group or a functional group. In the convergent method for making higher dPEGs, $R^1$ is generally going to be a protecting group.

The protecting groups that are preferred are those that can be easily made and easily deprotected. We prefer those which can be deprotected under a variety of conditions, including with acid, with reduction, usually under hydrogen with a Pd/C catalyst or with Ra/Ni, with fluoride ion, and with DDQ or cerium ammonium nitrate and the like.

The particular preferred protecting groups which can be removed with acid include, for example: tetrahyropyran-2-yl (THP), TMB (2,4,6-trimethylbenzyl), 4-alkoxybenzyl-, 3,4-dialkoxybenzyl, trityl, trimethylsilyl, t-butyl-dimethylsilyl and others known in the art. Further preferred are the THP and TMB protecting groups, and the most preferred is the THP group.

Those groups that are preferred generally are removed reducing conditions that include both a metal catalyst and hydrogen at various convenient pressure or with a Raney/Ni reducing system. The preferred protecting groups which fall in this group, which are reduced with hydrogen and a catalyst, include, for example, the following: benzyl, TMB, PMB and p-alkoxybenzyl, DMB and 3,4-dialkoxybenzyl. Those removed under reducing conditions with Ra/Ni include TMB, benzyl and PMB and p-alkoxybenzyl and not DMB or 3,4-dialkoxybenzyl.

Those preferred groups that are removed with fluoride ion are predominated the trisubstitued silyl protecting group, especially the trimethylsilyl, t-butyldimethyl and diphenyl-t-butylsilyl. These are all produced from the least expensive and most readily available silyl chlorides. The preferred sources of fluoride ion include, for example, n-tetrabutylammonium fluoride trihydrate in THF; n-tetrabutylammonium bromide with potassium fluoride hydrate in THF; or potassium fluoride and 18-crown-6 in THF, and the like.

A special group of protecting groups is those that are removed with DDQ or cerium ammonium nitrate (CAN), preferably the latter. These are preferred for at least two reasons, one is their selectivity, which is discussed in more detail for the stepwise approach. This group of protecting groups includes ones from the grouping of the p-alkoxybenzyl and 3,4-dialkoxybenzyl protecting groups, where the alkyl of the alkoxy is from $C_1$-$C_{22}$, preferred $C_1$, $C_3$-$C_6$, $C_{12}$, $C_{18}$. In the convergent approach these can be removed with acid, hydrogen with catalyst or with CAN.

There are a variety of functional groups that can be included in $R^1$. For the convergent approach it is preferred that R1 is a functional group when equation 1 is the final step in producing the desired dPEG derivative.

The functional groups that are preferred include, but are not limited to the following: azide, protected amines, nitrile or cyano, protected carboxylic acids, protected thiols, including disulfides, and protected aldehydes. The azide is especially preferred since it can be cleanly reduced to the free amine with triphenyphosphine in dry THF, followed by hydrolysis.

The protecting group on the amine includes the CBZ, t-boc, benzyl and substituted benzyls, trityl, and others known in the art. The preferred embodiment of this invention for building up the dPEGs allows for a broader range of protecting groups which might otherwise be unstable in the presence of the compounds like that with the general structural formula I.

The nitrile or cyano functional group can be converted to the aldehyde, the free carboxylic acid or the free amine. It can also be added to the diol product using methods known in the art, e.g., addition of acrylonitrile or with cyano displacement to compounds with the general structural formula of II.

$R^1$ also can be from among the grouping of the protected carboxylic acids, where the acid is protected from the groupings that include those from the alkyl, especially sterically bulky and aralkyl, preferably the t-butyl and benzyl protecting groups. Again, the breadth of chemical sensitivity within the grouping may be considerably expanded due to the mild and rapid nature of the preferred embodiments for making dPEGs.

The functional grouping of the protected thiols, includes those from the aralkyl, acetyl, thiourea and others known in the art.

Processing options for the convergent approach additionally include, for example, chromatography as well as size exclusion and size selective techniques for purification of higher MW materials.

For the convergent method it may be necessary to use a molar ratio of the compound of formula I or XXII to the compound of formula II greater than 2:1 such that the reaction in equation (1) provides a mixture comprising an excess of the compound of formula I or XXII and the compound of formula III. An embodiment of this invention is to take advantage of the different solubility properties of compounds I and III to obtain a pure mixture of the desired product III. The processing method of the convergent method embodiment involves the following possible steps. Exactly how these steps are carried out and which protecting or functional group structure is preferred will depend on the values of x and 2x+y. First, contacting the above mixture of an excess of the compound of formula I or XXII and of compound of formula III with an organic medium and collecting the compound of formula III or VI from the organic medium after washing the said organic medium with an aqueous medium. The reactant I is more soluble in the water and so may be washed out much more easily. The choice of the preferred organic medium may be determined by the values of x and 2x+y. An alternative embodiment involves contacting the above mixture of an excess of the compound of formula I and of compound of formula III with an aqueous medium and collecting the compound of formula III or VI from the aqueous medium by extracting the aqueous medium with an organic medium once or multiple times. The said organic medium can then be washed with water to remove any remaining compounds of structural formula I. This process can be repeated to recover more of the compound of formula III or VI by extracting the aqueous with an organic, washing the organic with a "fresh" aqueous medium. The preferred choices of the organic media are chosen from methylene chloride, ethyl acetate, t-butyl methyl ether or toluene and mixtures thereof. Also, in order to control the solubilities of I and III in the aqueous medium adding the following may help the efficiency of this process by controlling the solubility of compounds I or compound III relative to their solubility in the organic medium. The preferences/variables for the aqueous medium include no additives/salts or additives/salts. The salts/additives can include, but are not limited to NaCl, $CaCl_2$, $NH_4^+Cl^-$, and ammonium sulfate.

An additional embodiment of this processing step is when $R^1$ is a protecting group or functional group whose hydrophobicity can be increased as the value of x and 2x+y increases. The hydrophobicity is adjusted such that the partition coefficient of the compounds of structural formula III is in favor of the organic remaining the same relative to the compounds of structural formula I and XXII as the value of x and 2x+y increases.

A further preferred embodiment comprises the use of protecting groups such as the various benzyl derivatives, including benzyl, TMB, 4-alkoxybenzyl, and 3,4-dialkoxybenzyl. These can be used as hydroxy protecting groups, as well as protecting groups for the amine, thiol and carboxylic acid functional groups various embodiments.

A further embodiment allows one to combine the strengths of the convergent and stepwise approaches to making larger MW heterobifunctional dPEGs. A compound with the general structural formula III, with a higher value of 2x+y, can be mono protected with an appropriate protecting group, e.g., TMB, THP or Bn. This compound of general structural formula can be combined with a MW compound with a functional group or protecting group, different from structural formula, to give the precise and desired MW of dPEG with can easily converted to the heterobifunctional derivative.

The alkoxybenzyl compounds as protecting groups are very interesting due to their high selectivity with a variety of other protecting groups and even with other alkoxybenzyl groups. These properties allow them to be very attractive to the stepwise approach and which is well documented in the cited references. They are also removed under a variety of conditions including mild acid or reduction conditions.

Additionally, the alkoxybenzyl derivatives are useful in aiding in the processing of the dPEGs due to the range of compounds that can be made and the concomitant hydrophobicity range of these compounds as protecting groups. Their precursors, the cresols and catechols are very inexpensive, as are the alkyl bromides used to convert them to the alkoxy benzyl derivatives. The latter are available and inexpensive as the straight chain bromides from $C_2$ up to at least $C_{22}$. The alkoxy derivatives are easily made by refluxing the catechol, e.g., 4-methylcatechol, or cresol, e.g., p-cresol, with the alkylbromide in acetone in the presence of powdered potassium carbonate for about 2 hours. The alpha-methyl group is converted to either the benzyl chloride or bromide by methods well known in the art and attached to the dPEGs to make the key intermediates of the general structural formula like XXII.

A further and special embodiment of the convergent method involves a method to make a wide variety of heterogeneous dPEGs. Shown below are several general embodiments of this embodiment. The reactants are combined in solution and the ionizing agent is added to produce the product, similarly to the methods for the homogeneous dPEGs.

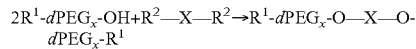

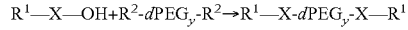

where, X is an aliphatic, aromatic, aliphatic-aromatic organic linker moiety optionally substituted with heteroatoms. X also may contain oxyethylene or dPEG units or moieties.

The intermediates, $R^1$—X-$dPEG_y$-X—$R^1$ and $R^1$-$dPEG_x$-O—X—O-$dPEG_x$-$R^1$, where $R^1$ is a hydroxyl protecting group, are convertible into HO—X-$dPEG_y$-X—OH and HO-$dPEG_x$-O—X—O-$dPEG_x$-OH, respectively, and may be cycled back through the convergent method, similarly with the method above for making the homogeneous dPEGs. These examples are intended to be exemplary and not limiting to the application of this invention.

$R^1$-$dPEG_x$-O—X—O-$dPEG_x$-$R^1$, for example, is convertible into $R^1$-$dPEG_x$-O—X—O-$dPEG_x$-$OR^2$, which then can be incorporated as an intermediate in the stepwise approach or as a branch chain in building heterogeneous branched dPEG systems.

X is incorporated into the dPEG backbone with heterogeneity to compliment the physical, physical chemical and physiological properties of the dPEG infrastructure.

B. Stepwise Approach to Synthesize Heterobifunctional dPEGs

This embodiment uses the same general methods for selectively and rapidly producing dPEG compounds, except the goal is to directly produce a final product that can be selective built up or directly converted into useful heterobifunctional dPEG compounds. Detailed and preferred embodiments of the stepwise approach to dPEGs, equation (2):

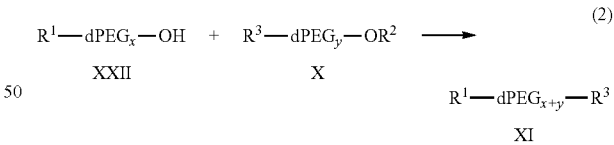

In equation (2), for $R^1$ and $R^3$ generally are either both different hydroxyl protecting groups or one is a functional group and the other a protecting group, with $R^1$ and $R^3$ always being different. It is preferred that until the desired value of x+y is achieved, that both $R^1$ and $R^3$ not be functional groups, whereas both $R^1$ and $R^3$ can both be and preferably are different protecting groups. It also is preferred that, while $R^1$ and $R^3$ are different, that it is possible to deprotect $R^1$ or $R^3$ in the presence of the other.

To build up a higher value of x+y, when $R^1$ or $R^3$ is a hydroxyl protecting group in compound XI, $R^1$ or $R^3$ is specifically (if the other is FG) or selectively (if both are protecting groups) removed to produce the compounds of general structural formulas XII and XIII respectively.

$$\text{HO-}d\text{PEG}_{x+y}\text{-R}^3 \quad \text{XII}$$

$$\text{R}^1\text{-}d\text{PEG}_{x+y}\text{-OH} \quad \text{XIII}$$

Compounds of formulas XII and XIII are reacted with the appropriate reagents, preferably tosyl chloride and triethylamine, to produce the compounds of formulas XIV and XV, wherein $R^2$ is a leaving group by convention, as in equation (2)

$$\text{R}^1\text{-}d\text{PEG}_{x+y}\text{-OR}^2 \quad \text{XIV}$$

$$\text{R}^3\text{O-}d\text{PEG}_{x+y}\text{-R}^2 \quad \text{XV}$$

$$\text{HO-}d\text{PEG}_{x+}\text{-R}^3 + \text{R}^1\text{-}d\text{PEG}_{x+y}\text{-OR}^2 \rightarrow \text{R}^1\text{-}d\text{PEG}_{2x+2y}\text{-R}^3 \quad (3')$$

These steps can be continued until the desired value of x+y or 2x+2y is achieved. It is preferred that the total value of oxyethylene moieties be not substantially more than about 1000.

When the desired value of x+y or 2x+2y is achieved, the products will exist where (a) $R^1$ and $R^3$ are different hydroxyl protecting groups, (b) $R^1$ or $R^3$ is a functional group and the other a hydroxyl protecting group, or (c) both $R^1$ and $R^3$ are functional groups. The next objective is to convert these compounds to other compounds that have the desired functionality for the intended application or is a building block for a branching dPEG system. Hence one can use the methods available in the art to convert the situations found above in (a), (b) and (c) into (i) a heterobifunctional compound using methods well known in the are of organic functional group transformations (see Table 1), (ii) form linear dPEGs like m-dPEGs with a single reactable functionality, or XXVII where one end is deprotected, where the resulting hydroxyl containing dPEG can be used directly or converted to the tosylate and used as a branching component in the embodiment of this invention for making branched dPEG systems.

Table 1 summarizes some of the preferred combinations of $R^1$ and $R^3$. These tabulations are not meant to be limiting, but rather representative of some of the more useful functionality used in many biological applications. The entries in the table below are intended to be representative and not limiting of the scope of the invention.

TABLE 1

Examples of Selectivity in the Deprotection of Compound XI

| | $R^1$ | $R^3$ | Reagent | Selectivity | Condition |
|---|---|---|---|---|---|
| 1 | $N_3$ | THP | PPTS | THP | a |
| 2 | $N_3$ | TMB | TFA | TMB | a |
| 3 | $N_3$ | $SiR_3$ | $F^-$ | $SiR_3$ | a |
| 4 | THP | benzyl | $H_2$, Pd/C | benzyl | b |
| 5 | THP | TMB | $H_2$, Pd/C | TMB | b |
| 6 | Benzyl | DMB/PMB | CAN | DMB/PMB | b |
| 7 | CBZ—NH— | THP | PPTS | THP | a |
| 8 | CBZ—NH— | THP | $H_2$, Pd/C | CBZ—NH— | a |
| 9 | t-boc—NH | Benzyl | $H_2$, Pd/C | Benzyl | a |
| 10 | THP | thiourea | PPTS | THP | c |
| 11 | THP | thiourea | PPTS | THP | c |
| 12 | Thioacetate | benzyl | $H_2$, Pd/C | Benzyl | a |
| 13 | Alkyl ester | THP | PPTS | THP | a |
| 14 | Alkyl ester | Benzyl | $H_2$, Pd/C | Benzyl | a |
| 15 | t-butyl ester | $N_3$ | TFA | t-butyl ester | d |
| 16 | $N_3$ | t-boc—NH— | HCl | t-boc—NH— | d |
| 17 | Thioacetate | $N_3$ | Base | Thioacetate | d |
| 18 | CBZ—NH— | t-butyl ester | $H_2$, Pd/C | CBZ | d |
| 19 | CBZ—NH | t-butyl ester | TFA | t-butyl ester | d |

The protecting groups that are preferred are those that can be easily made and easily deprotected. Those groups that can be deprotected under a variety of conditions are preferred, including with acid, with reduction (usually under hydrogen with a Pd/C catalyst or with Ra/Ni), with fluoride ion, and with DDQ or cerium ammonium nitrate, and the like. These preferences have been detailed above for the convergent method.

In contrast to the convergent approach, where both ends of the resulting $dPEG_{2x+y}$ are the same and the goal is to quickly and mildly remove the protecting groups, for the stepwise method the goal is to achieve a high level of selectivity in treating $R^1$ in the presence of $R^3$ and vice versa. This applies to the situations outlined below. One skilled in the art is referred to key references in the field by Greene and Kocienski for a full perspective of the options that may be available in practicing this invention.

It should be understood, however, there are certain protecting groups that are more useful and, hence, more preferred than maybe others concerning their selectivity. As an example, the THP protecting group is very stable to base and to reduction with $H^2$, Pd/C and so groups like the general benzyls, including CBZ, can be removed selectively in its presence. The THP group can be taken off with very mild acid, preferably pyridinium p-toluene sulfonate (PPTS) in the presence of other groups that require much stronger acids, e.g., the TMB (with TFA in the presence of benzyl), and the t-butyl ester. Of course the silyl protecting groups can specifically taken off with fluoride, but also have some acid sensitivity and have been reported to be removable with higher pressures of hydrogen, so while very selective should be removed preferentially. The p-alkoxy and 3,4-dialkoxy-benzyl protecting groups can be removed both with acid and with $H_2$, Pd/C, but have high selectivity over other benzyls and even within the various alkoxybenzyls when deprotected with DDQ or CAN. These alkoxybenzyls can act also as hydrophobic handles to control or modify the solubility of intermediates, to make them easier to isolate and purity form starting materials and the usual by-products.

Functional groups, such as azido and cyano, are quite stable under most of the non-reducing conditions, especially the azido group, which is stable to both strong acid and base. The azido group is very useful as a kind of protected functional group, as is can easily be reduced to the amine with triphenylphosphine.

The range of preferred functional groups and protecting groups for the stepwise approach are the same as for the convergent approach, and these are specified above in the detailed description of the convergent method. However, the need for selectivity requires delineating some of the preferences for combinations of $R^1$ and $R^3$ in the stepwise approach. Some specific examples are shown in Table 1.

When deprotecting compound XI, there are three selectivity options for the deprotecting reagent to achieve to making either compound XII, HO-$dPEG_{x+y}$-$R^3$, or compound XIII, $R^1$-$dPEG_{x+y}$—OH. The fourth option, (d) is included for completeness in the situation where $R^1$ and $R^3$ are different functional groups and one or both are protected.

(a) Deprotection of protecting group $R^3$ in the presence of a functional group $R^1$:

$$\text{R}^1\text{-}d\text{PEG}_{x+y}\text{—R}^3 + \text{reagent} \rightarrow \text{R}^1\text{-}d\text{PEG}_{x+y}\text{-OH}$$

where, $R^1$=FG; $R^3$=PG (b) Selective deprotection of protecting group in the presence of another:

$$\text{R}^1\text{-}d\text{PEG}_{x+y}\text{-R}^3 + \text{reagent} \rightarrow \text{R}^1\text{-}d\text{PEG}_{x+y}\text{-OH}$$

where, $R^1$=PG; $R^3$=PG $$\text{R}^1\text{-}d\text{PEG}_{x+y}\text{-R}^3 + \text{reagent} \rightarrow \text{HO-}d\text{PEG}_{x+y}\text{-R}^3$$

where, $R^1=PG$; $R^3=PG$ (c) Deprotection of protecting group $R^1$ in the presence of functional group $R^3$ $$R^1\text{-}dPEG_{x+y}\text{-}R^3 + \text{reagent} \rightarrow HO\text{-}dPEG_{x+y}\text{-}R^3 \qquad 5$$

where, $R^1=PG$; $R^3=FG$ (d) Selective deprotection of the protected functional group, when $R^1$ and $R^3$ are both functional groups.

As stated above, Table 1 exemplifies different reaction strategies for making compounds usefully made in accordance with the precepts of the present invention.

In another preferred embodiment, the strengths of the convergent and stepwise approaches is in making larger MW heterobifunctional dPEGs. A compound with the general structural formula III, with a higher value of 2x+y, can be mono protected with a preferred protecting group, e.g., TMB, THP, PAB, DAB. The compound of general structural formula XXXXIII, $R^1$-$dPEG_{2x+y}$-OH, can be combined with a compound of general structural formula X, whose functional group or protecting group configuration has been selected to achieve the final functionality of the desired application and especially to give the single and desired MW of dPEG, can then be easily converted to the heterobifunctional derivative.

Also, any of these intermediates from the stepwise approach with the hyroxyl function on one terminus, free or converted to a leaving group, preferably the tosylate, and a functional group, reactable or not reactable, e.g., alkoxy, on the other, are useful and preferred building blocks in making the branched systems

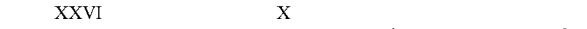

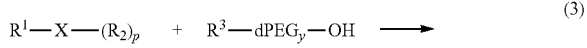

Refer to the detailed description of the particular and preferred protecting and functional groups in the convergent method.

Processing preferences exist for the stepwise approach, especially compared to the convergent approach detailed above. It is important not only to have the clean and efficient chemistry embodiments of this invention, but also to have efficient ways to purity the desired dPEG product from reactions that may require the use of an excess of one or the other reactant in equation (2), as well as removing the normal by-products of these displacement reactions. In contrast to the convergent approach, where the compound of general structural formula XXII may be left in excess at the conclusion of the process, in the stepwise approach the option may be to use either XXII or X in excess, as well as to perform a deprotection in the final mixture.

For the stepwise approach there are at least options for optimal stoichiometry. One is to have X in slight excess and the other is to have XXII in slight excess. These are only options to the preferred case, where one may titrate the reaction to an endpoint where little detectable amounts of either reactant XXII or X are present with the product XI. However, it is nearly impossible to eliminate both reactants completely, so these processing preferences can still be taken advantage of in the routine processing of reaction (2). There also is an advantage when the product mixture is put through the deprotection process prior to a final purification process.

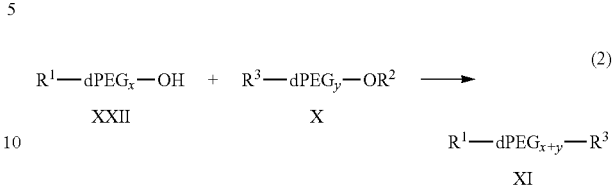

There are then four options for reaction (2): (a) excess of formula XXII without deprotection; (b) excess of formula XXII with deprotection; (c) excess of formula X without deprotection; and (d) excess of formula X with deprotection. The final mixtures, accordingly, are shown below:

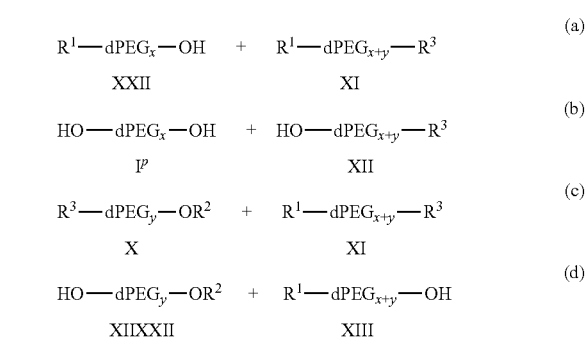

An embodiment of this invention is to take advantage of the difference and range of solubility properties of the two compounds in each situation described above for (a)-(d) in aqueous versus organic media. This embodiment is described above for the convergent method. In that case there is only one stoichiometric option, and the option of further removing the protecting groups does not exist when using an extractive work-up. However, for dPEGs where the value of 2x+y is large, the resultant diols may be separated by techniques that differentiate by size and properties based on size. Also, certain hydrophobic properties in the protecting groups and functional groups can be taken advantage of in order to control the differences in these solubility properties. This latter embodiment is taught above for the convergent method, but applies to the stepwise approach as well.

Of the options (a)-(d), (b) may be the option which produces a mixture that is most easily differentiated based on solubility differences. Hence, a preferred embodiment of the invention is to take the mixture comprising an excess of compound XXII and the product compound XI, and remove the protecting group $R^1$ with the appropriate reagent. During the work up, the resulting mixture of the $dPEG_x$ diol, I$^p$, and compound of the structural formula XII is dissolve in an organic solvent. The mixture in the organic solvent then is washed with an aqueous solution, one or more times to remove the excess of the dPEGx diol, to leave a pure mixture of compound XII in the organic medium. It may be necessary to extract the combined aqueous washes if compound XII has any appreciable aqueous solubility. The process may be optimized with the proper choice of the organic solvent and the ionic strength of the aqueous washes.

The preferred choices of organic medium are chosen from methylene chloride, ethyl acetate, t-butyl methyl ether, toluene or mixtures thereof. The preferred choices of salts and additives to the aqueous phase to aid in controlling or optimizing the partition coefficients of compounds of general structural formulas I$^p$ and XII, include the following: sodium chloride, calcium chloride, ammonium chloride, ammonium sulfate and the like known in the art.

A special embodiment of the present invention relates to the protecting groups, $R^1$ or $R^3$, or where the protecting portion of a functional group, $R^1$ or $R^3$, is a group whose hydrophobicity can be increased as the values x, y, and x+y increase. This is the same embodiment as above for the convergent method.

A further and special embodiment of the stepwise method involves a method to make a wide variety of heterogeneous dPEGs. Shown below are several general embodiments of this embodiment. The reactants are combined in solution and the ionizing agent is added to produce the product, similarly to the methods for the homogeneous dPEGs.

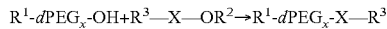

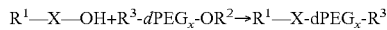

The intermediates, $R^1$-dPEG$_x$-X—$R^3$ and $R^1$—X-dPEG$_x$-$R^3$, can have $R^1$ or $R^3$ selectively converted and cycled further through the stepwise process, incorporating other heterogeneity or homogeneous dPEG portions of the linear chain, and can then or at this stage be converted to the entire range of heterobifunctional and heterogeneous dPEGs. The intermediates like HO-dPEG$_x$-X—$R^3$ and $R^1$—X-dPEG$_x$-OH, but not limited to, can also be components and branches for branched heterogeneous dPEGs.

Branching dPEGs

This embodiment employs at least two methods for selectively making specific discrete polyethylene glycol (dPEG) compounds containing a discrete and predetermined number of ethylene oxide moieties, moieties that are incorporated into branching systems. These two preferred embodiments are outlined in equations (3) and (4).

$$R^1{-}X{-}(OH)_p + R^3{-}dPEG_y{-}OR^2 \longrightarrow \quad (3)$$
$$\text{XXVI} \qquad\qquad\quad \text{X}$$
$$R^1{-}X{-}(dPEG_y{-}R^3)_p$$
$$\text{XXVII}$$

$$R^1{-}X{-}(R^2)_p + R^3{-}dPEG_y{-}OH \longrightarrow \quad (4)$$
$$\text{XVII} \qquad\qquad \text{XVIII}$$
$$R^1{-}X{-}(dPEG_y{-}R^3)_p$$
$$\text{XXVII}$$

The methods for this embodiment in equations (3) and (4) are similar to the convergent and stepwise methods described above in a number of ways.

In one preferred embodiment reacting a first reactant having the general structural formula XXII $$R^1{-}X{-}(OH)_p \qquad\qquad \text{XXVI}$$

with a second dPEG compound having the general structural formula X $$R^3\text{-}dPEG_y\text{-}OR^2 \qquad\qquad \text{X}$$

in the presence of an ionizing compound capable of ionizing dPEG compound XXII reactant and under reaction conditions to produce said dPEG compound having the general structural formula III $$R^1{-}X{-}(O\text{-}dPEG_y R^3)_p \qquad\qquad \text{III}$$

where, dPEG represents a discrete (OCH$_2$CH$_2$) moiety, each $R^1$ independently is a functional group (FG) or protecting group (PG); y ranges from about 1 to 300, $R^2$ is a leaving group, $R^1$ is a functional group or protecting group and is different than $R^3$, and y ranges from about 1 to 300; X is a difunctional organic moiety which may be substituted with one or more hetero substituents and may contain hydroxy functionality and a dPEG spacer moiety; p ranges from 2 to about 9; preferably less than 4. The structures below show some examples of compound XXVI.

The preferred embodiment for reacting XXVI with X to give compound XXVII is to add the ionizing agent, preferably potassium t-butoxide, at the same rate or slower then the species like or $R^1{-}X{-}(OH)_{p-1}(dPEG_x\text{-}R^3)$, $R^1{-}X{-}(OH)_{p-2}(dPEG_x\text{-}R^3)_2$, and so on, are being formed. This embodiment does not allow for a reactive species, such as $R^1{-}X{-}(O^-M^+)(OH)_{p-1}$, $R^1{-}X{-}(O^-M^+)(OH)_{p-2}(dPEG_x\text{-}R^3)$, and so on, to have a chance to build up and cause unwanted side reactions. The may allow the invention to be practiced with a wider range of functional groups and protecting groups for $R^1$ and $R^3$. Also in this embodiment it is not practical or allowable to pre-generate the species. $R^1{-}X{-}(O^-M^-)_p$. Other bases, such as the butyl lithiums and lithium diisopropyl amines, also can be used in this embodiment.

Below are shown are a few practical examples of X. These were chosen due to their availability and potential for being very cost effective foundations upon which to build branched dPEG systems.

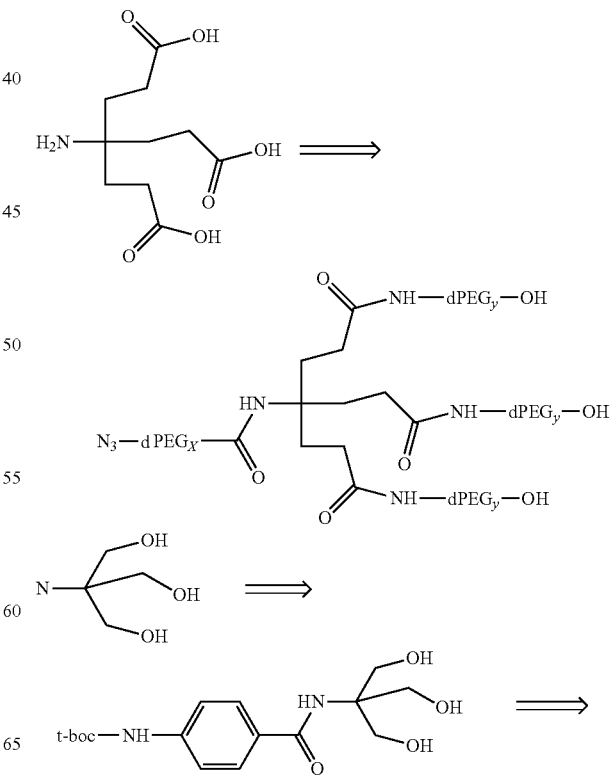

-continued

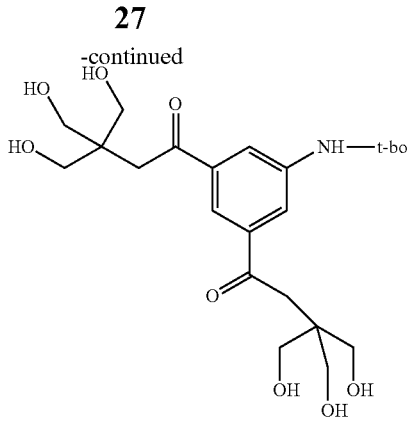

One can also have $R^1$—X—$(R^2)_p$ reacting with $R^3$-$dPEG_y$-OH in the presence of an ionizing agent to make the compound of structural formula III. Depending on the particular structures having the option may be advantageous.

Therefore, in a second preferred embodiment reacts a first reactant having the general structural formula XVII $$R^1—X—(R^2)_p \quad\quad XVII$$

with a second dPEG compound having the general structural formula XVIII $$R^3\text{-}dPEG_y\text{-OH} \quad\quad XVIII$$

in the presence of an ionizing compound capable of ionizing dPEG compound XVIII reactant and under reaction conditions to produce said dPEG compound having the general structural formula XXVII $$R^1—X—(O\text{-}dPEG_yR^3)_p \quad\quad XXVII$$

wherein dPEG represents a discrete $(OCH_2CH_2)$ moiety, each $R^1$ independently is a functional group (FG) or protecting group (PG); y ranges from about 1 to 300, $R^2$ is a leaving group, $R^1$ is a functional group or protecting group and is different than $R^3$, and y ranges from about 1 to 300; X is a difunctional organic moiety which may be substituted with one or more hetero substituents and may contain hydroxy functionality and a dPEG spacer moeity; p ranges from 2 to about 9; preferably less than 4. The structures below show some examples of $R^1$—X—$(OH)_p$.

The preferred structures for $R^1$, $R^2$ and $R^3$ are the same as for the convergent and stepwise methods described above and, particularly, the preferences for $R^1$ and $R^3$ to either a functional group or protecting group and must be different. These are described in detail above for the stepwise approach.

Once compound XXVII is formed, a further embodiment of the invention is to continue to build addition branching onto that present in compound of general structural formula XXVII. For example, higher branching systems can be formed. For example, $R^1$ in III can converted to (if functional group) or de-protected (if protecting group) to give the hydroxy containing XIX, which when reacted with the species $R^1$—X—$(R^2)_{p'}$, XX, in the presence of an ionizing agent such as potassium t-butoxide, as shown below, in the equation gives compound of structural formula XXI. P may be equal to or different than p', and the species XX can contain a dPEG linker which contains the terminal leaving group.

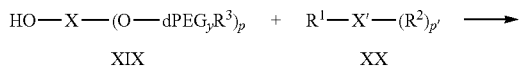

-continued
$$R^1—X'—(X—(O—dPEG_yR^3)_p)_{p'} \quad\quad XXI$$

This reaction can be continued to produce even higher branched systems with the same or other building blocks. For example, the intermediate XXI can be selectively deprotected and the hydroxyl converted to a leaving group to produce a compound of general structural formula XXX, and then reacted with the compound of structural formula XXVI under the preferred methods of this invention to give compound of structural formula XXXI, which now contains p X p X p branches, as set forth below.

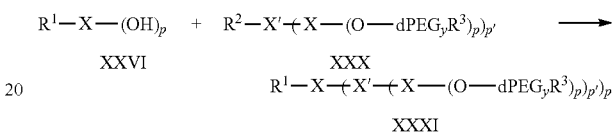

Structures with the general structural formula like XXI and XXXI with p X p' and p X p' X p branches, where $R^3$ is either a functional group or a hydroxyl protecting group, the hydroxyl group of which is convertible to a functional group, either of which is reactable with a T, may be converted to branched structures like those shown in the general structural formulas XXXII and XXXIII below.

$$R^1—X'—(—X—(O\text{-}dPEG_yT)_p)_{p'} \quad\quad XXXII$$

$$R^1—X—(—X'—(—X—(O\text{-}dPEG_yT)_p)_{p'})_p \quad\quad XXXIII$$

An alternative embodiment is for $R^1$ in the structures with the general formulas like XXXI and XXXIII to be selectively removed and converted to a functional group or where $R^1$ is a functional group which are reactable with T may be converted to branched structures of the general structural formulas like XXXIV and XXXV.

$$T\text{-}X'—(—X—(O\text{-}dPEG_yR^3)_p)_{p'} \quad\quad XXXIV$$

$$T\text{-}X—(—X'—(—X—(O\text{-}dPEG_yR^3)_p)_{p'})_p \quad\quad XXXV$$

See the scheme below for an example of the above approach to branched dPEGs. The sequence can be continued to higher branching. A preferred method for building up the branched systems is to keep the ratio of 1:p as low as possible, allowing for the reactions to go easily to completion. It is known in the art, that as 1:p becomes larger, it is more and more difficult to achieve complete conversion of reactants to the single desired product without using large excesses of the singly reactable compound.

As part of the scheme below, a dPEG spacer has been used to achieve some distance from the branch point in order to maintain a high level of reactivity in building up the branching. Though Frechet has shown that even without a spacer one can still achieve generation G5 without the yields of each step dropping appreciably (Reference: M. Jayaraman and J. M. J. Frechet, *J. Amer. Chem. Soc.*, 120, 12996-12997 (1998).

This dPEG spacer may be made by first deprotecting XXVII at $R^1$ and then reacting this with a compound of structural formula X. In the scheme compound of formula X is a species where $R^3$=THP and $R^2$ is tosylate and x=4.

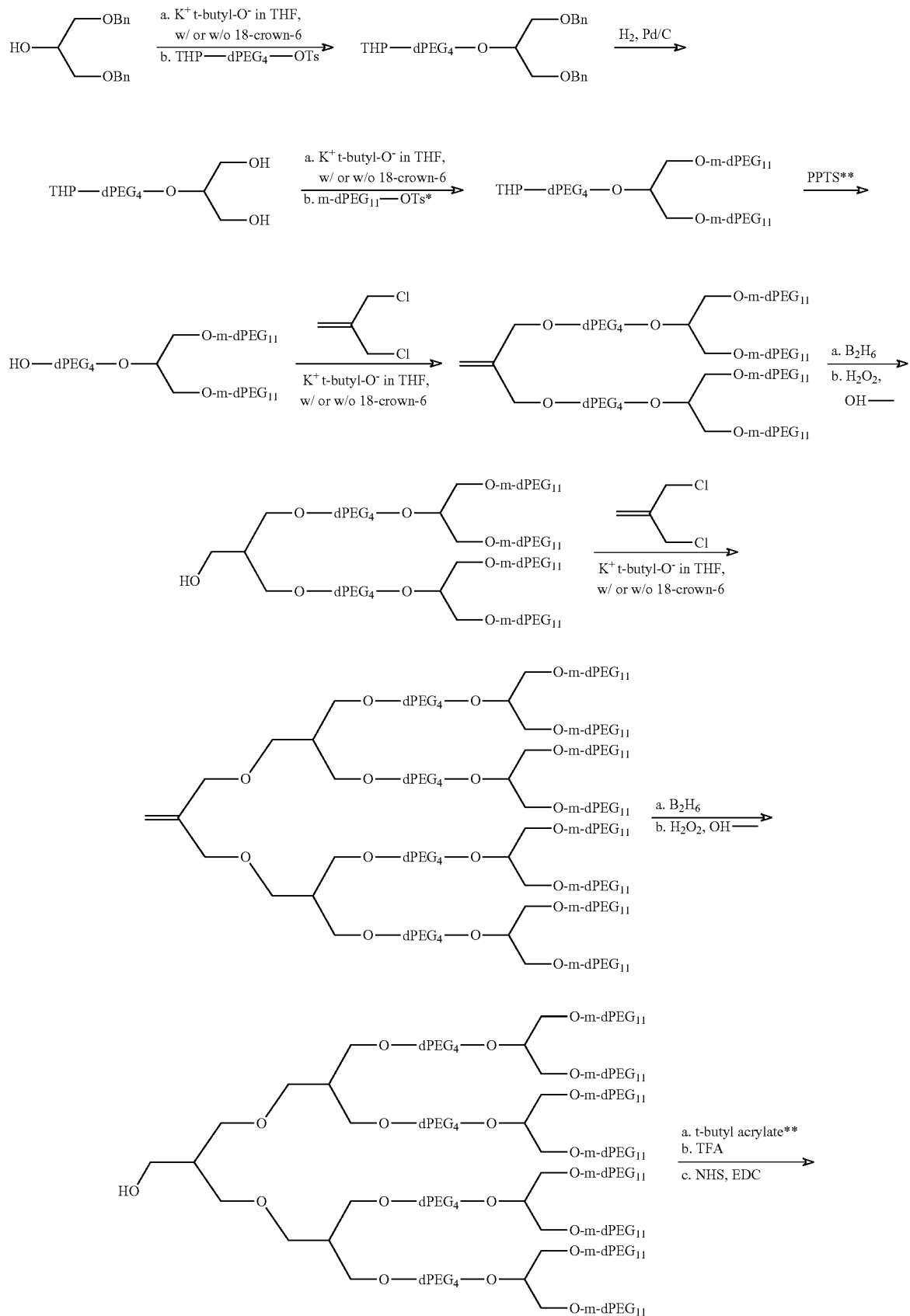

-continued

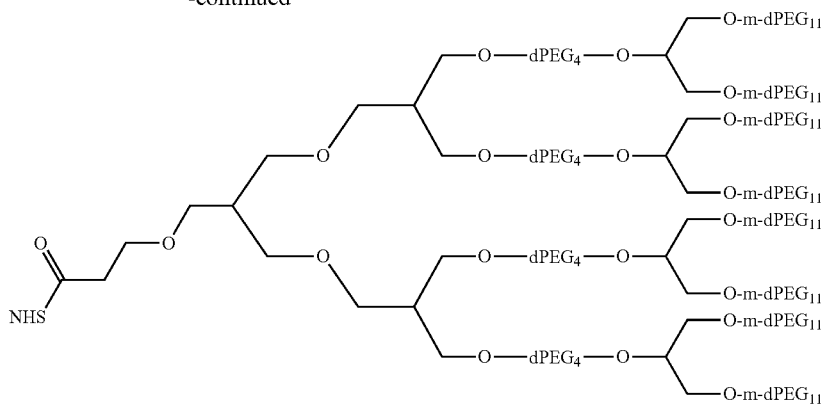

*this can be any general
TsO—dPEG$_x$—FG/PG
**Any of the branched alcohols, e.g., 2 or 4 above can also be converted to active ester; the alcohols can also be converted to the amine or thiol, the amine to the maleimide; also, an additional dPEGx spacer can be added as well..

An important aspect of this invention is the utility of using a combination of the three methods, the convergent, the stepwise, and branching, to achieve the diversity of compounds which are desirable in the area of making and modifying, but not limited to, biologically active compounds.

A further embodiment of this invention provides the option of coupling together two different or two of the same branching systems. For example, if $R^1$ of the product from the equation above is a hydroxyl protecting group, it can be deprotected and reacted with a species like XXI in the presence of an ionizing reagent, preferably potassium t-butoxide to produce another branched dPEG system.

HO—X'—(—X—(O-dPEG$_y$R$^3$)$_p$)$_{p'}$+R$^2$O-dPEG$_x$-X—(O-dPEG$_y$-R$^3$)$_p$→(R$^3$-dPEG$_y$-O)$_p$—X-dPEG$_x$-X'—(—X—(O-dPEG$_y$R$^3$)$_p$)$_{p'}$

As described in the embodiments of the convergent and stepwise methods, a variety of intermediates described therein can be used a heterogeneous dPEG branches in building up parts of branched dPEG systems.

Functional Group Manipulation

An important aspect of this invention is to provide valuable dPEG compounds that are precursors to other compounds that can be used in a variety of biological applications. To be valuable in the particular application, $R^1$ and $R^3$ undergo functional group manipulation to achieve the functionality which is desirable for the particular application of the linear or branch dPEG that has been constructed using a combination of one or more of the convergent, stepwise and branched embodiments of this invention.

Below is Table 2 that shows (a) what basic functional group manipulation can be performed at $R^1$ and $R^3$, where if either is a protected hydroxyl group has been deprotected according to the preferred embodiments of this invention, in order to convert each or both to the many valuable functionalities for a diverse range of biological applications; and (b) the resulting functionalities representative those that are most widely used in combination for attachment and incorporation of dPEGs in the diversity of technological applications. To those skilled in the art, it is apparent that some combinations are not chemically compatible, and these are excluded. Some combinations will accommodate the role as crosslinker or spacer, and other applications requiring two different reactable functionalities, while many are useful where only one end is reactable and the other is inert to the application. Applications where the dPEG may be used strictly a solution or immunological property modifier, for surface coating applications, while others can be valuable as delivery agents. All of these examples are given only to represent some of the options, but not to limit the scope of the invention in any way.

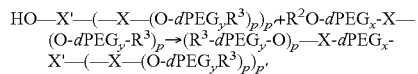

Linear dPEGs         Branched dPEGs

A—dPEG$_a$—B    or    A—X—(dPEG$_a$B)$_p$

TABLE 2

Key Functional Group Conversions from $R^1$ and $R^3$ to A and B

| Entry | Intermediate from $R^1$ or $R^3$ | Reagent | Final FG and Options for A and B |
|---|---|---|---|
| 1 | Azide; N$_3$ | Ph$_3$P | Amino; NH$_2$ |
| 2 | OH | (a)TsCl; (b) N$_3$; c) Ph$_3$P | Amino; NH$_2$ |
| 3 | OH | ClCH$_2$CH(C$_2$H$_5$)$_2$; base | acetal |
| 4 | OH | (a) thioacetate; (b) base | thiol |
| 5 | OH | (a) t-butyl acrylate, base; (b) TFA; (c) NHS, EDC | Active ester |
| 6 | OH | Disuccinimidyl dicarbonate | Active carbonate |
| 7 | CN | DIBAH | aldehyde |
| 8 | NH$_2$ | MPS | maleimide |
| 9 | NH—CBZ | H2, Pd/C | amine |
| 10 | NH—t-boc | TFA or HCl | amine |
| 11 | S—COCH$_3$ | base | thiol |
| 12 | NH$_2$ | Fmoc—Cl | Protected amine for peptide synthesis |
| 13 | OH | CH$_3$X; X = OTs, I | methoxy |
| 14 | t-butyl ester | TFA | acid |
| 15 | t-butyl ester | (a) TFA; (b) t-butyl carbazate; (c) HCl | hydrazdie |
| 16 | NH$_2$ | various | isocyanate |
| 17 | NH$_2$ | thiophosgene | thioisocyanate |
| 18 | NH$_2$ | Iodoacetic acid | iodoacetyl |
| 19 | NH$_2$ | SPDP | thiopyridyl |
| 20 | OH | Various | phosphoramidites |

Preferred combinations of A and B in heterobifunctional compounds include, inter alia, the following:

a. A=amine; B=carboxyl and derivatives, esters, active esters
b. A=amine; B=hydroxyl and derivatives, phosphoramidites; active carbonates, and the like
c. A=thiol; B=hydroxyl and derivatives, like b.
d. A=thiol; B=carboxyl and derivatives, like a.
e. A=amine; B=thiol
f. A=maleimide; B=carboxyl and derivatives, like a.
g. A=aldehyde or equivalent; B=carboxyl and derivatives, like a.
h. A=aldehyde or equivalent; B=thiol
i. A=thiol; B=alkoxy and the like
j. A=amine; B=alkoxy
k. A=carboxyl and derivatives; B=alkoxy
l. A=aldehyde or equivalent; B=alkoxy
m. A=maleimide; B=alkoxy
n. A=carboxylic acid, active ester; B=carboxyl ester.

As used herein, T is a biologically active molecule and can be selected from a therapeutic, diagnostic or other active moieties, such as, for example targeting molecules. T is added onto the novel dPEG molecules of the present invention by techniques well known in the art. Representative "T" moieties include those chemical entities that:

1) carry diagnostic and/or therapeutic radionuclides;
2) are diagnostic and/or therapeutic photoactive molecules;
3) are chemotherapeutic agents, or precursors or prodrugs thereof;
4) are protein toxins or derivatives thereof;
5) target tumors through a variety of receptor modalities;
6) bind with biologically active proteins;
7) cause the molecule to be excluded from cells;
8) allow the molecule to enter cells; or
9) cause it to target infections.

More specifically, the "T" moiety may be, for example, a molecule chelated to or bound with a radionuclide (e.g., I-123, I-125, I-131, In-111, Y-90, At-211, Bi-213, etc); a photoactive group (e.g., dansyl, fluorescein, cyanocobalamin, cyanine dye, porphyrin, etc.); a drug (e.g., dehydrotestosterone, adriamycin, vincristine, 5-fluorouracil, etc.); a cancer targeting agent (e.g., monoclonal antibody or fragment, growth factor, signaling peptide, etc.); an MRI active agent (e.g., chelated gadolinium (Gd), fluorinated compounds, boron-11 compounds, etc); a neutron activated molecule (e.g., boron-10 containing molecules, Gd containing molecules, etc.); or a membrane crossing agent (e.g., tranferrin, folate, cyanocobalamin, etc.).

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference The following tables show examples of experiments that could be done using the convergent method and using intermediates generated from the convergent method to selectively make heterobifunctional compounds, III, using the stepwise method described in this invention. These examples are representative and are not limited to those listed in the tables.

TABLE 3

Using the Convergent Method for Building Higher MW dPEGs, eq. (1)

| Experiment No. | I(x) | II(y) | III (2x + y) | $R^1$ | $R^2$ |
|---|---|---|---|---|---|
| 1 | 12 | 12 | 36 | TMB, THP, Bn | OTs |
| 2 | 36 | 36 | 108 | TMB, THP, Bn | OTs |
| 3 | 108 | 108 | 324 | TMB, THP, p-alkoxybenzyl | OTs |
| 4 | 36 | 12 | 84 | THP, TMB | OTs |
| 5 | 12 | 36 | 60 | THP, TMB | OTs |
| 6 | 12 | 4 | 28 | THP, TMB | OTs |
| 7 | 324 | 324 | 972 | THP, TMB, p-alkoxy, 3,4-dialkoxybenzyl | OTs |

TABLE 4

Using the Stepwise Approach with Intermediates from Convergent Method (eq. (2))

| Exp. # | I(x) | X(y) | XI(x + y) | $R^1$ | $R^3$ | $R^2$ |
|---|---|---|---|---|---|---|
| 8 | 8 | 12 | 20 | $N_3$ | THP | OTs |
| 9 | 12 | 8 | 20 | THP, TMB | $N_3$ | OTs |
| 10 | 36 | 11 | 47 | THP, TMB | $CH_3$ | OTs |
| 11 | 36 | 20 | 56 | THP | $N_3$ | OTs |
| 12 | 20 | 11 | 31 | THP, TMB, p-alkoxybenzyl | $CH_3$ | OTs |
| 13 | 108 | 11 | 119 | THP, TMB, p-alkoxybenzyl | $CH_3$ | OTs |
| 14 | 12 | 20 | 32 | $N_3$ | $CO_2$-t-butyl | OTs |
| 15 | 12 | 12 | 24 | thioacetate | $CO_2$-t-butyl | OTs |
| 16 | 12 | 8 | 20 | $N_3$ | —NH—CBZ | OTs |

EXPERIMENTAL PROCEDURES

General. Solvents and chemicals were obtained from commercial sources (Sigma-Aldrich Chemical Co., Acros Organics-Fisher Scientific Co.). The solvents were analytical grade or better and were used without further purification, except $Et_3N$ was purified by refluxing over phthalic anhydride for 1 h followed by distillation, then redistilled from CaH. Methylene chloride and THF were dried over molecular sieve (Fisher 3A) prior to use. Silica gel chromatography was done with 70-230 mesh 60 A silica gel (Fisher Scientific Co.).

Spectral Analyses. All $^1$H NMR were obtained on either a Bruker Avance DPX-400 MHz or a Varian 400 MHz instrument. Mass spectral data were obtained on either (1) a VG Analytical (Manchester, England), VG-70SEQ mass spectrometer with associated 11250J Data System using fast atom bomdardment (FAB$^+$) at 8 keV in a matrix of MeOH/DMIX (thioglycerol/DMSO/TFAA:90/9/1) or 3NBA (3-nitrobenzyl alcohol) or (2) a PerSeptive Biosystems Mariner Electrospray Time of Flight Mass Spectrometer (ESI-TOF). For ES$^+$ analysis, the samples were dissolved in 50/50 MeOH/$H_2O$ and were introduced by an integral syringe infusion pump.

Example 1

Preparation of TMBO-dPEG$_{20}$-OTMB or bis-(O-TMB)-dPEG$_{20}$

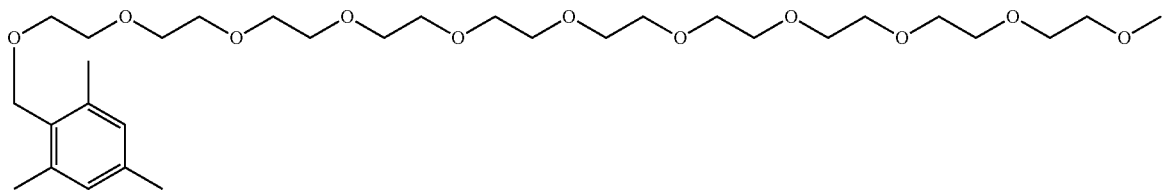

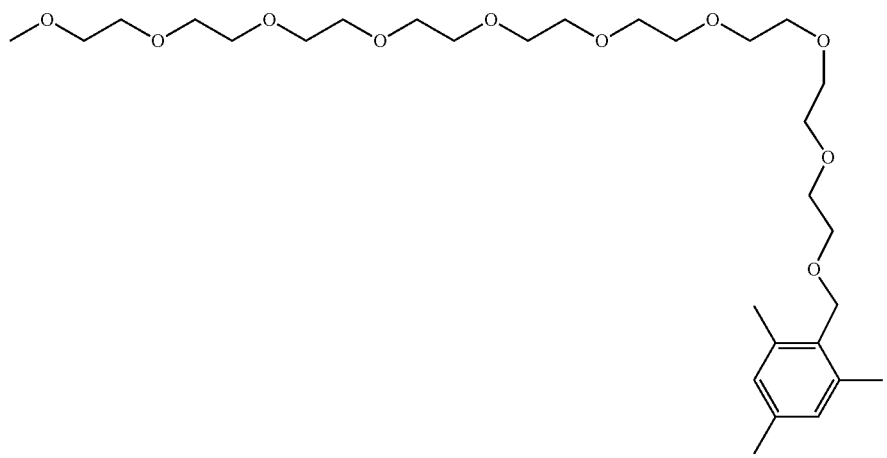

C$_{60}$H$_{106}$O$_{21}$
Exact Mass: 1162.72
Mol. Wt.: 1163.47
C, 61.94; H, 9.18; O, 28.88

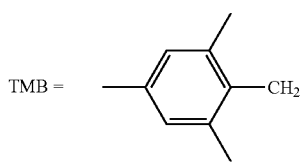

TMB =

95% Sodium hydride (3.5 g, 0.14 mole) was placed into a 1 L flask under argon and dry THF (300 mL) at −25° C. was added. Dry TMBO-dPEG$_8$OH (52.3 g, 0.10 mole) was added slowly over about 20 minutes. The pot temperature was maintained below 15° C. bis-O-tosyl-dPEG$_4$ was dissolved in THF (200 mL) and added slowly to pot. The reaction mixture was allowed to stir for 17 h as it warmed to rt. The reaction was monitored by tlc vs TMBO-dPEG$_8$OH, eluting with 10% MeOH/CH$_2$Cl$_2$. The reaction was complete; the starting material was used up. The reaction mixture was filtered through a celite cake filter prepared with CH$_2$Cl$_2$. The filtrate was concentrated in vacuo; the resulting oil was extracted with CH$_2$Cl$_2$ (2×200 mL) and 10% (aq) NaCl (300 mL). The CH$_2$Cl$_2$ layer was isolated, dried over MgSO$_4$, filtered and concentrated in vacuo to leave an oil. A column was prepared with 600 g of silica gel and hexane as needed. The crude product was placed onto column with hexane and a minimum of t-butylmethyl ether (TBME, 100 mL) was used to make a clean transfer. The column was eluted with hexane (4 L) and then as follows: (2 L) 20% TBME/hexane; (2 L) 30% TBME/hexane;

(2 L) 40% TBME/hexane; (2 L) 50% TBME/hexane; (2 L) 1% MeOH/TBME;

(4 L) 5% MeOH/TBME. Like fractions containing product were combined and concentrated in vacuo to give 40.7 g (72%). The product was characterized by nmr. $^1$H NMR[400 MHz, DMSO(d$_6$)] ☐6.85 (s, 4H), 4.46 (s, 4H), 3.58 (t, 8H), 3.54 (s, 72H), 3.01 (s, 12H), 2.22 (s, 6H). HRMS calcd for C$_{60}$H$_{106}$O$_{21}$ (M+Na)$^+$: 1185.7124.
Found: 1185.7133.

Comments:

The above preparation of the bis-(O-TMB)-dPEG$_{20}$ is an example of the convergent approach to build up larger dPEGs.

The bis-tosylate of dPEG₄ is reacted with a mono protected octaethylene glycol, namely, TMBO-dPEG₈OH. This reaction scheme gives a bis-O-(TMB-dPEG₂₀).

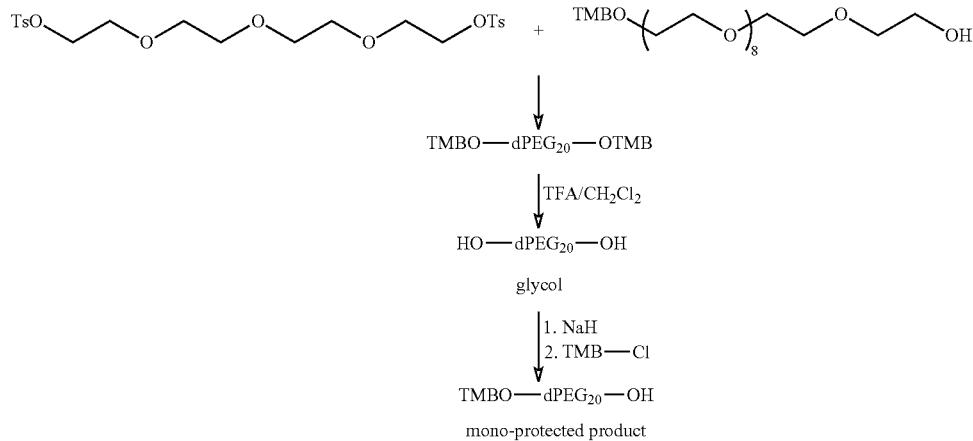

Example 2

Preparation of eicosylethylene glycol (HO-dPEG₂₀-OH)

product were combined and concentrated in vacuo to give 5.5 g (32%). The product was characterized by nmr. ¹H NMR [400 MHz, CDCl₃] δ4.50-3.88 (b, 2H), 3.9-3.4 (m, 80H).

Comments:

bis-(O-TMB)-dPEG₂₀ is cleaved by acid under anhydrous conditions to give eicosyltheylene glycol (HO-dPEG₂₀-OH).

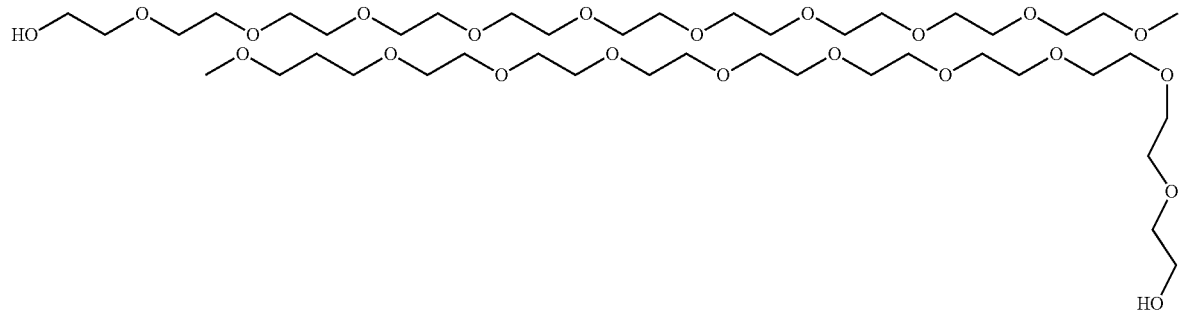

C₄₀H₈₂O₂₁
Exact Mass: 898.53
Mol. Wt.: 899.07
C, 53.44; H, 9.19; O, 37.37 bis-(O-TMB)-dPEG₂₀ (22.4 g, 1.9×10⁻³ mole) was placed into a 1 L flask under argon and dry CH₂Cl₂ (300 mL) at 0° C. Flask and contents were maintained at about 0° C. for 4 h while TFA (100 mL) dissolved in CH₂Cl₂ (200 mL) was added drop wise. The reaction progress was monitored by tlc on silica gel plates eluting with TBME. The reaction was complete in about 4 h; the TMB group was cleaved no starting material was present. The solvent was removed in vacuo to leave 47.0 g of crude oil product. A column was prepared with 600 g of silica gel and hexane as needed. The crude product was placed onto column with hexane; a minimum of t-butyl-methyl ether (TBME, 30 mL) was used to make a clean transfer. The column was eluted with hexane (4 L) and then as follows: (12 L) 50% TBME/hexane; (2 L) 10% MeOH/TBME; (2 L) 30% MeOH/TBME. Like fractions containing The latter is a useful. For example, it can be mono-protected as shown below to give TMBO-dPEG₂₀-OH.

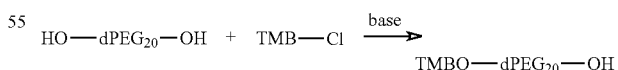

The latter can be further elaborated by reacting with the bis-tosylate, TsO-dPEG₂₀-OTs, in a convergent sense to give TMBO-dPEG₆₀-OTMB.

One can also elongate TMBO-dPEG₂₀-OH. The latter is converted to metal alkoxide which is then reacted with N₃-dPEG₄OTs, to give N₃-dPEG₄O-dPEG₂₀OTMB. The latter can be reduced using Ph₃P and water or Pd/C in presence of H₂. In either case, one gets the H₂N-dPEG₂₄-OTMB. The latter is converted to Cbz-NH-dPEG₂₄-OTMB. The TMB group is cleaved with acid under anhydrous conditions to give Cbz-NH-dPEG$_{24}$-OH. The hydroxyl function is converted to the ester with t-butyl acrylate to give Cbz-NH-dPEG$_{24}$-OCH$_2$CH$_2$CO$_2$-t-bu. The Cbz group is cleaved with Pd/C in the presence of H$_2$ to give the amino-dPEG-t-butyl ester, H$_2$N-dPEG$_{24}$-OCH$_2$CH$_2$CO$_2$-t-bu. We will see and example of latter in the next experiment procedure.

The HO-dPEG$_{20}$-OH is also used to make diacids or HO-dPEG$_{20}$-OCH$_2$CH$_2$CO$_2$-t-butyl. One simply react the glycol with t-butyl acrylate to give diester, t-bu-O$_2$C—CH$_2$CH$_2$O-dPEG$_{20}$-OCH$_2$CH$_2$CO$_2$-t-bu, the t-butyl groups are cleave by acid to give the diacid, HO$_2$C—CH$_2$CH$_2$O-dPEG$_{20}$-OCH$_2$CH$_2$CO$_2$H. The hydroxy-dPEG$_{20}$-t-butyl ester is prepared simply by reacting excess HO-dPEG$_{20}$-OH with minimal t-butyl acrylate. The same procedure we use to prepare the HO-dPEG$_4$-t-butyl ester. The higher homologues, hydroxy-dPEG$_{20}$-t-butyl ester are extremely important compounds.

uct were combined and concentrated in vacuo to give 40.3 g (57% yield). Product was characterized by nmr. $^1$H NMR[400 MHz, DMSO(d$_6$)] □6.8 (s, 2H), 4.48 (s, 2H), 3.78-3.67 (m, 2H), 3.60-3.48 (m, 46H), 2.28 (s, 6H); 2.19 (s, 3H).

Comments:

The above is a precursor to the following compounds: H$_2$N-dPEG$_{12}$-OTMB; Cbz-NH-dPEG$_{12}$-OTMB; Cbz-NH-dPEG$_{12}$-OH; Cbz-NH-dPEG$_{12}$-OCH$_2$CH$_2$CO$_2$-t-bu; H$_2$N-dPEG$_{12}$-OCH$_2$CH$_2$CO$_2$-t-bu; H$_2$N-dPEG$_{12}$-OH; H$_2$N-dPEG$_{12}$-OCH$_2$CH$_2$CO$_2$H.

Note: The amino alcohol comes from the reducing the Cbz group of Cbz-NH-dPEG$_{12}$-OH in the presence of Pd/C and H$_2$. The H$_2$N-dPEG$_{12}$-OH produced is converted to boc-NH-dPEG$_{12}$-OH, which in turn is converted to boc-NH-dPEG$_{12}$-OCH$_2$CH$_2$CO$_2$-t-bu. The ester function is converted into the carboxylic acid via saponification and neutralization with an equivalent of acid under anhydrous conditions at 0° C. to give boc-NH-dPEG$_{12}$-OCH$_2$CH$_2$CO$_2$H.

Reaction:

Example 3

Preparation of Azido-dPEG$_{12}$-OTMB

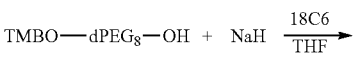

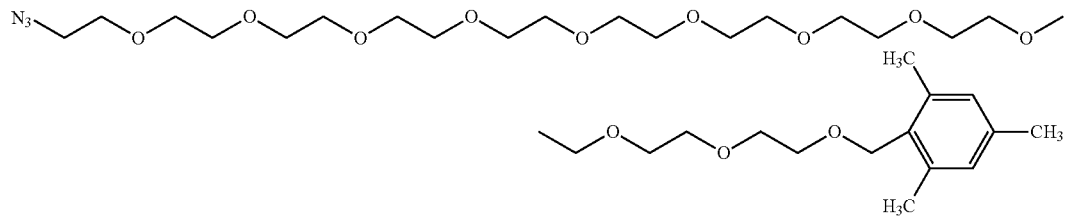

C$_{34}$H$_{61}$N$_3$O$_{12}$
Exact Mass: 703.43
Mol. Wt.: 703.86
C, 58.02; H, 8.74; N, 5.97; O, 27.28

95% Sodium hydride (3.5 g, 0.14 mole) was placed into a 1 L flask under argon and THF (200 mL) and 18C6 (4.4 g) was added at rt. TMBO-dPEG$_8$OH (50 g, 0.10 mole) dissolved in dry THF (75 mL) was added to pot at RT. There was an evolution of hydrogen gas. The addition took about 3 hr with stirring. After a total of 50 minutes, N$_3$-dPEG$_4$OTs (38.6 g, 0.10 mole) dissolved in THF (75 mL) was added. The reaction mixture was stirred for about 17 h at rt under argon. The reaction solution was monitored by tlc on silica gel plates, eluting with 10% MeOH/CH$_2$Cl$_2$ vs. N$_3$-dPEG$_4$OTs. The reaction was about 90% complete. Therefore, DMAC (75 mL) was added and the reaction was heated under reflux for about an hour. The reaction was complete by tlc, that is, all the N$_3$-dPEG$_4$OTs was used up and only one new product was observed. A column was prepared with silica gel (600 g) and hexane (6 L) as needed. The crude product was pre-absorbed on silica gel (100 g) and placed onto the column. The column was eluted with hexane (4 L), and then as follows: (2 L) 20% TBME/hexane; (4 L) 30% TBME/hexane; (2 L) 40% TBME/hexane; (4 L) 50% TBME/hexane; (2 L) 60% TBME/hexane; (2 L) 80% TBME/hexane; (4 L) TBME, and 2% MeOH/CH$_2$Cl$_2$; 5% MeOH/CH$_2$Cl$_2$. Like fractions containing prod- -continued

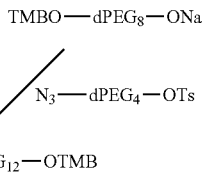

N$_3$-dPEG$_{12}$-OTMB can be elongated further after cleavage of the TMB group with anhydrous TFA in CH$_2$Cl$_2$. The resulting azido alcohol can be tosylate, N$_3$-dPEG$_{12}$-OTs, and reacted with the alkoxide, TMBO-dPEG$_8$-ONa, to give the TMBO-dPEG$_{20}$-N$_3$. This reaction sequence can be repeated indefinitely to give higher and higher homologues. See the reaction scheme below.

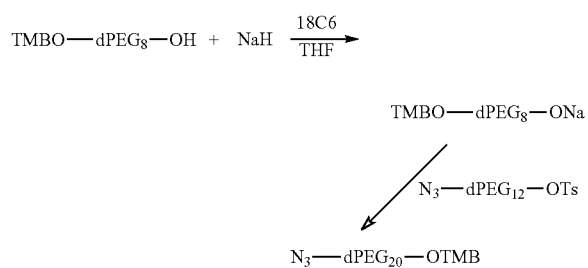

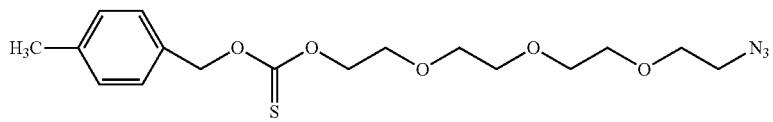

Comments:

Cbz-amino-dPEG$_5$ azide is an excellent product because it can be reduced to the diamine, H$_2$N-dPEG$_5$NH$_2$ with Pd/C in the presence of hydrogen. This implies that we can make higher homologues as well. One can reduce the azido group with Ph$_3$P/water to give Cbz-NH-dPEG$_5$-NH$_2$. The latter can be reacted with boc$_2$O to give Cbz-NH-dPEG$_5$-HN-boc. One can cleave the Cbz group by hydrogenolysis to give the mono-protected diamine, namely, boc-NH-dPEG$_5$-NH$_2$.

Example 5

Preparation of 4-O-Tosyl-dPEG$_4$ azide

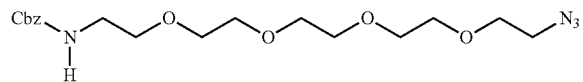

C$_{16}$H$_{25}$N$_3$O$_6$S
Exact Mass: 387.15
Mol. Wt.: 387.45
C, 49.60; H, 6.50; N, 10.85; O, 24.78; S, 8.28

Example 4

Preparation of Cbz-amino-dPEG$_5$ azide

Cbz-NH-CH$_2$CH$_2$-O-CH$_2$CH$_2$-O-CH$_2$CH$_2$-O-CH$_2$CH$_2$-O-CH$_2$CH$_2$-N$_3$

C$_{18}$H$_{28}$N$_4$O$_6$
Exact Mass: 396.20
Mol. Wt.: 396.44
C, 54.53; H, 7.12; N, 14.13; O, 24.21

95% Sodium hydride (3.0 g, 0.12 mole) was placed into a 1 L flask under argon and THF (200 mL) and 18C6 (4.6 g) was added at rt. Cbz-NHCH$_2$CH$_2$OH (22.2 g, 0.11 mole) dissolved in dry THF (75 mL) was added to pot at rt. There was an evolution of hydrogen gas. The addition took about ½ h with stirring. After a total of 50 minutes, N$_3$-dPEG$_4$OTs (34.4 g, 0.90 mole) dissolved in THF (75 mL) was added. The reaction mixture was stirred for about 17 h at rt under argon. The reaction solution was monitored by tlc on silica gel plates, eluting with 10% MeOH/CH$_2$Cl$_2$ vs N$_3$-dPEG$_4$OTs. The reaction was about 90% complete. Therefore DMAC (75 mL) was added and the reaction was heated under reflux for about an hour. The reaction was complete by tlc, that is, all the N$_3$-dPEG$_4$OTs was used up and only one new product was observed by tlc. The solvent was removed in vacuo to leave an oil. The latter was extracted with CH$_2$Cl$_2$ and water. The organic layer was separated, dried over MgSO$_4$, filtered and concentrated in vacuo to an oil (47.8 g).

HO-dPEG$_4$-N$_3$ (50.0 g, 0.23 mole) was placed into a 500 mL flask under argon with CH$_2$Cl$_2$ (100 mL). The flask and contents were cool to about 0° C. TsCl (47.3 g, 0.25 mole) was add plus CH$_2$Cl$_2$ (50 mL). Et$_3$N (40 mL) dissolved in CH$_2$Cl$_2$ (50 mL) was added to pot drop wise over about an hour. The reaction mixture was stirred for about 17 h while allowing it to warm to rt under argon. The reaction solution was monitored by tlc on silica gel plates, eluting with 10% MeOH/CH$_2$Cl$_2$ vs N$_3$-dPEG$_4$OH. The reaction was complete by tlc, that is, all the N$_3$-dPEG$_4$OH was used up and only one new product was observed. The CH$_2$Cl$_2$ layer was washed with water, separated, dried over MgSO4, filtered and concentrated in vacuo to leave an oil. A column was prepared with silica gel (600 g) and hexane (6 L) as needed. The crude product was pre-absorbed on silica gel (125 g) and placed onto the column. The column was flashed with hexane (6 L). Then, the column was eluted by gravity as follows: (4 L) 20% TBME/hexane; (4 L) 30% TBME/hexane; (2 L) 50% TBME/hexane, and (2 L) TBME. Like fractions containing product were combined and concentrated in vacuo to give 73 g (82% yield). Product was characterized by nmr. $^1$H NMR[400 MHz, DMSO(d$_6$)] □7.80 (d, 2H), 7.48 (d, 2H), 4.21 (t, 2H), 3.75-3.65 (m, 2H), 3.63-3.43 (m, 12H); 3.40 (t, 2H); 2.45 (s, 3H).

Example 6

Preparation of 2,4,6-trimethylbenzyltetraethylene glycol (TMBO-dPEG$_4$-OH)

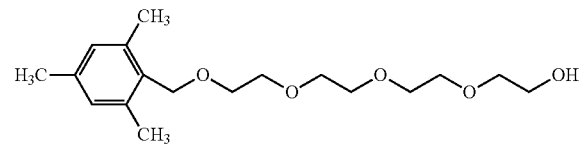

C$_{18}$H$_{30}$O$_5$
Exact Mass: 326.21
Mol. Wt.: 326.43
C, 66.23; H, 9.26; O, 24.51

-continued

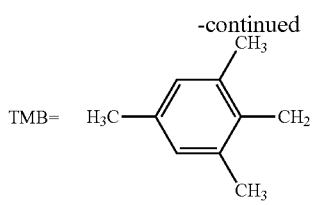

95% Sodium hydride (40.85 g, 1.6 moles) was placed into a 3 L flask under argon and THF (1.2 L) at −10° C. was added. Dry tetraethylene glycol (500.0 g, 2.57 moles) was added slowly. The pot temperature was maintained below 15° C. during the addition. Once the NaH had reacted, a homogeneous solution resulted. 18C6 (3.9 g) and dimethyl-acetamide (DMAC, 500 mL) was added. Chloroisodurene (TMB-Cl, 98.6 g, 0.58 mole) dissolved in THF (500 mL) was added to pot over about 4 h. The reaction mixture was stirred for about 17 h at about 40° C. under argon. The reaction was monitored by tlc on silica gel plates, eluting with 10% MeOH/$CH_2Cl_2$ vs TMB-Cl. The reaction was complete; the TMB-Cl was consumed. The solvent was removed in vacuo; the resulting oil was extracted with $CH_2Cl_2$ (700 mL) and water (300 mL). The $CH_2Cl_2$ layer was separated, dried over $MgSO_4$, filtered through fluted filter paper and concentrated in vacuo to leave an oil. A column was prepared with 600 g of silica gel and hexane as needed. The crude product was placed onto column with hexane and a minimum of t-butylmethyl ether (TBME, 100 mL) to make a clean transfer. The column was eluted with hexane (4 L) and then as follows: (2 L) 10% TBME/hexane; (2 L) 20% TBME/hexane; (4 L) TBME/hexane; (3 L) 40% TBME/hexane, and (2 L) TBME. Like fractions containing product were combined and concentrated in vacuo to give 140.2 g (73%). The product was characterized by nmr. $^1$H NMR[400 MHz, DMSO($d_6$)] □6.81 (s, 2H), 4.56 (t, 1H), 4.45 (s, 2H), 3.57-3.45 (m, 14H), 3.41 (t, 2H), 2.28 (s, 6H), 2.22 (s, 3H).

Example 7

Preparation of O-(13-(2',4',6'-trimethylbenzyl)-1,4,7,10,13-pentaoxapentadecyl)tosylate (TMBO-dPEG$_4$-OTs)

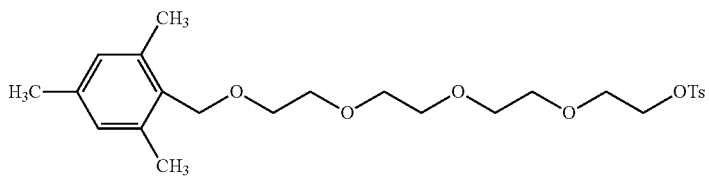

$C_{25}H_{36}O_7S$
Exact Mass: 480.22
Mol. Wt.: 480.62
C, 62.48; H, 7.55; O, 23.30; S, 6.67

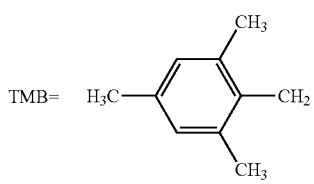

2,4,6-trimethylbenzyltetraethylene glycol (138.8 g, 0.43 mole) was dried by azeotrope with toluene, then it was placed into a 2 L flask under argon. $CH_2Cl_2$ (700 mL) was added, pot and contents were cooled to approximately −15° C. Tosyl chloride (86.0 g, 0.45 mole) was added, then $Et_3N$ (75 mL) was added drop wise over about 3 h while allowing the flask and contents to warm to rt over 17 h with stirring. The reaction was monitored by tlc using silica gel plates, eluting with t-butylmethyl ether (TBME). The reaction was complete by tlc, the TMBO-dPEG$_4$-OH had been converted to the tosylate. The reaction mixture was filtered on a Buchner funnel, filtrate was extracted with water (700 mL). The $CH_2Cl_2$ layer was separated, dried over $MgSO_4$, filtered and concentrated in vacuo to leave an oil. The latter was chromatographed on 600 g of silica gel. The column was prepared with hexane as needed. The crude product was placed onto column with hexane, used a minimum TBME (100 mL) to make a clean transfer to column. The column was eluted with 4 L hexane and then as follows: (2 L) 10% TBME/hexane; (4 L) 20% TBME/hexane; (2 L) 30% TBME/hexane; (2 L) 50% TBME/hexane and (4 L) TBME. Like fractions containing product were combined and concentrated in vacuo to yield 155.0 g (75%). The product was characterized by nmr. $^1$H NMR[400 MHz, DMSO($d_6$)] □7.78 (d, 2H), 7.45 (d, 2H), 6.80 (s, 2H), 4.45 (s, 2H), 4.08 (t, 2H), 3.62-3.40 (m, 14H), 2.40 (s, 3H), 2.29 (s, 6H), 2.20 (s, 3H).

Comments:

The TMBO-dPEG$_4$-OTs can be prepared from the TMBO-dPEG$_4$-OH without chromatography. This is a great savings because one eliminates one chromatography. Note: All trace impurities are removed during chromatography; an example of combining these two steps are given in the next two experiments that follow. The overall yield is 65% while stepwise process gives about 60% overall yield with two chromatographies.

In short, if one wants to make TMBO-dPEG$_8$-OTs as an example. It is better to react TMBO-dPEG$_4$-OTs with excess HO-dPEG$_4$-ONa to give TMBO-dPEG$_8$-OH. Do not chromatograph the latter, just tosylate to give TMBO-dPEG$_8$-OTs. If one wants pure TMBO-dPEG$_8$-OH, hundreds of grams are chromatographed easily on about 600 to 800 g of silica gel.

Example 8

Preparation of O-(13-(2',4',6'-trimethylbenzyl)-1,4,7,10,13-pentaoxapentadecyl)tosylate (TMBO-dPEG$_4$-OTs) from TetraEG without Chromatography of 2,4,6-trimethylbenzyl-tetraethylene glycol (TMBO-dPEG$_4$-OH)

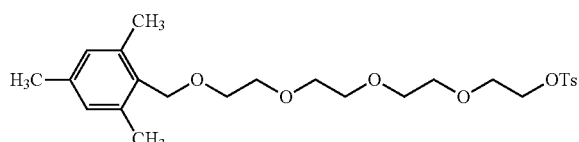

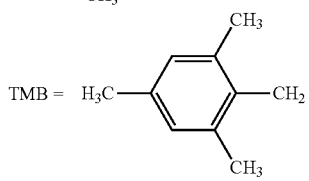

C$_{25}$H$_{36}$O$_7$S
Exact Mass: 480.22
Mol. Wt.: 480.62
C, 62.48; H, 7.55; O, 23.30; S, 6.67

95% Sodium hydride (54.5 g, 2.1 moles) was placed into a 3 L flask under argon; dry THF (1.5 L) at −15° C. was added to pot. Dry tetraethylene glycol (tetraEG, 543 g, 2.8 moles) was added while maintaining pot temperature below 15° C. There was an evolution of H$_2$ gas along with an exotherm. A homogeneous solution resulted once the addition was complete. TMB-Cl (198.2 g, 1.17 moles) dissolved in 800 mL of THF was added drop wise at rt over about 4 h. The reaction mixture was stirred vigorously for 17 h. The reaction was monitored by tlc using silica gel plates and eluting with 10% MeOH/CH$_2$Cl$_2$ and with TBME. The reaction was complete; all the TMB-Cl was consumed. The solvent was removed in vacuo; the resulting oil was extracted with water (700 mL) and 2×500 mL CH$_2$Cl$_2$. The organic layer was separated, dried over MgSO$_4$, filtered and concentrated to yield an oil (426 g). It is the same as the authentic material by tlc. The crude product [2,4,6-trimethylbenzyltetraethylene glycol (TMBO-dPEG$_4$-OH)] was dried by azeotrope over toluene. Assumed 100% yield; carried on to the next step without chromatography.

Product from above (assume 100%, 1.17 moles) was placed into 3 L flask with CH$_2$Cl$_2$ (1 L) and TsCl (237.6 g, 1.2 moles) under argon. Purified Et$_3$N (175 mL) was added all as once. The reaction was stirred at rt for 17 h under argon. The progress of the reaction was followed by tlc. The reaction mixture was tlc on silica gel plates and eluting with t-butyl-methyl ether (TBME). All the starting material was gone, or used up. The reaction mixture was washed with water (300 mL) 2×. The CH$_2$Cl$_2$ layer was isolated and dried over MgSO$_4$, filtered and concentrated in vacuo, the resulting oil weighs 556.9 g. A column was prepared with 900 g silica gel, and hexane as needed. The crude product was placed onto column with the same and a minimum TBME to make a clean. The column was eluted with 5 L of hexane and then as follows: (6 L) 20% TBME/hexane; TsCl came off column, then (2 L) 40% TBME/hexane, TBME until all of the product was off the column. Like fractions containing product were combined and concentrated in vacuo to give 397.3 g of crude product. It's approximately 90% pure by tlc. This material was rechromatographed using 800 g silica gel, and hexane as needed. The crude product (397.3 g) was placed onto column with hexane as needed, used column about 75 mL of TBME to make a clean transfer to column. The column was eluted with hexane (5 L) and then as follows: (2 L) 10% TBME/hexane; (2 L) 20% TBME/hexane; (2 L) 30% TBME/hexane; (2 L) 40% TBME/hexane; (4 L) 50% TBME/hexane; (2 L) 60% TBME/hexane; (4 L) 70% TBME/hexane, and (2 L) 80% TBME/hexane. Like fractions containing product were combined and concentrated, the product which is an oil weighs 363.8 g (65% overall yield). The NMR was consistent with the proposed structure. $^1$H NMR[400 MHz, DMSO(d$_6$) 7.77 (d, 2H), 7.47 (d, 2H), 6.80 (s, 2H), 4.48 (s, 2H), 4.12 (t, 2H), 3.60-3.53 (m, 14H), 2.45 (s, 3H), 2.28 (s, 6H), 2.20 (s, 3H).

Example 9

Preparation of 2,4,6-trimethylbenzyloctaethylene glycol (TMBO-dPEG$_8$-OH)

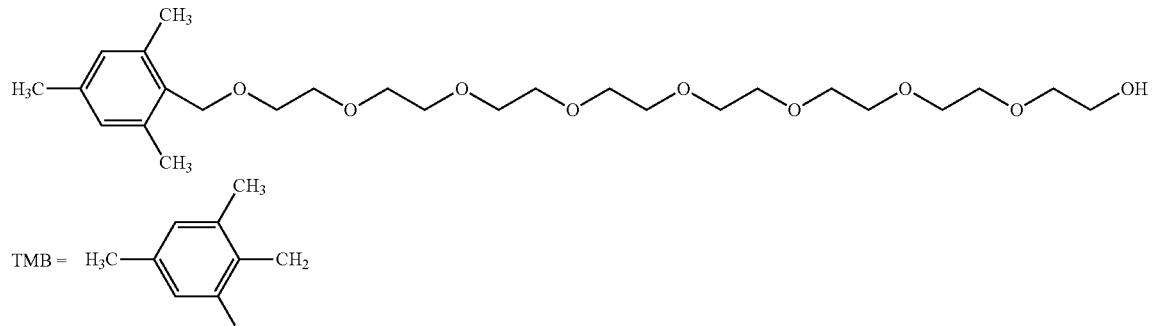

C$_{26}$H$_{46}$O$_9$
Exact Mass: 502.31
Mol. Wt.: 502.64
C, 62.13; H, 9.22; O, 28.65

95% Sodium hydride (27 g, 1.1 moles) was placed into 2 L flask under argon. dimethylacetamide (DMAC, 1 L) was cooled to approximately 0° C., and added to the reaction flask.

Dry tetraethylene glycol (345 g, 1.78 mole) was placed into a gas venting dropping funnel and added to reaction pot. Do not allow pot temperature to exceed 25° C. during the addition. There is an evolution of $H_2$ gas. When the addition was complete, a homogeneous solution resulted. 18C6 (6.5 g) was added, followed by the addition of 2,4,6-trimethylbenzyltetraethylene glycol (145.0 g, 0.30 mole) dissolved in DMAC (200 mL) and added drop wise over approximately 2.5 h at rt. The reaction mixture was allowed to stir at rt for 17 h. The reaction was monitored by tlc on silica gel plates, eluting with TBME. The tlc was run reaction on mixture vs starting material (ECC-007-29) on silica gel plates. The tlc plates were visualized with aid of UV lamp @ 254 nm. The starting material was converted to the product, so the reaction was worked up. The DMAC was removed in vacuo at about 40° C. and 0.1 mm Hg. The resulting oil was extracted with $CH_2Cl_2$ (700 mL), water (300 mL) and aqueous saturated NaCl solution (300 mL). The $CH_2Cl_2$ layer was isolated, dried over $MgSO_4$ and filtered through a celite cake in a glass center fritted Buchner funnel. The filter cake was prepared by slurring celite (about 50 g) in $CH_2Cl_2$ (200 mL), used $CH_2Cl_2$ as needed to make a clean transfer. The filtrate was concentrated in vacuo to leave an oil. A column was prepared using silica gel (600 g) and hexane as needed. The crude product was placed onto column with hexane as needed and minimum TMBE (100 mL) to make a clean transfer. The column was eluted as follows: (4 L) hexane; (4 L) 20% TBME/hexane; (2 L) 40% TBME/hexane; (2 L) 50% TBME/hexane; (6 L) TBME. Like fractions containing product were combined to give a yield of 120.2 g (79.7%). Product was characterized by nmr. $^1$H NMR[400 MHz, DMSO($d_8$)] □6.82 (s, 2H), 4.55 (t, 1H), 4.45 (s, 2H), 3.42-3.57 (m, 32H), 2.28 (s, 6H) 2.18 (s, 3H). Purity by quantitative nmr: 99.7%, internal std is bis-(4-trichloromethyl)benzene.

Comments:

TMBO-dPEG$_8$-OH can be converted to octaethylene glycol by cleaving the TMB group with TFA in $CH_2Cl_2$. The octaethylene glycol is readily converted to diacid $HO_2$C-dPEG$_8$-$CO_2$H via the bis-t-butyl ester, t-bu-$O_2$C-dPEG$_8$-$CO_2$-t-butyl. Note: the t-butyl groups are cleaved by TFA to give the diacid.

Example 10

Preparation of 4-O-(benzyl)tetraethylene glycol (PhCH$_2$O-dPEG$_4$-OH)

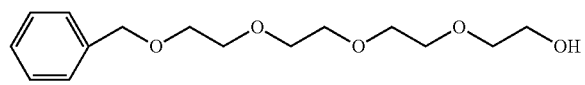

C$_{15}$H$_{14}$O$_5$
Exact Mass: 284.16
Mol. Et.: 284.35
C, 63.36; H, 8.51; O, 28.13

95% Sodium hydride (50 g, 2.0 moles) was placed into 3 L flask under argon; THF (1 L) at −20° C. was added to pot under argon. Dry tetraethylene glycol (tetraEG, 466.4 g, 2.4 moles) was added while maintaining pot temperature below 15° C. There was a evolution of $H_2$ gas with an exotherm. A homogeneous solution resulted once the addition was complete. 18C6 (7.5 g) was added. The benzyl bromide was dissolved in dimethylacetamide (DMAC, 500 mL), and placed into a gas venting dropping funnel and added over approximately 4 h. The pot temperature was maintained at about 5° C. with an ice bath. The reaction mixture was stirred for 17 h while allowing pot to warm to rt. Reaction mixture progress was monitored by tlc on silica gel plates vs benzyl bromide, eluting with EtOAc, Rf$_{product}$=0.27. The benzyl bromide was converted to product. Reaction mixture was filtered through a celite cake in a glass center fritted Buchner funnel, used $CH_2Cl_2$ as needed to make a clean filtration. Filtrate was concentrated in vacuo and the resulting oil was washed with water (500 mL) and extracted 2× with 500 mL $CH_2Cl_2$. The latter was dried over $MgSO_4$, filtered, and concentrated in vacuo to give an oil (374.5 g). A column was prepared using silica gel (600 g) and hexane as needed. The crude product was placed onto column with hexane as needed and minimum TMBE (100 mL) to make a clean transfer. The column was eluted as follows: (4 L) hexane; (4 L) 20% TBME/hexane; (2 L) 40% TBME/hexane; (2 L) 50% TBME/hexane; (6 L) TBME. Like fractions containing product were combined to yield 265.8 g (86%), same as authentic material by tlc.

Example 11

Preparation of 4-O-(benzyl)tetraethylene glycol (PhCH$_2$O-dPEG$_4$-OH)

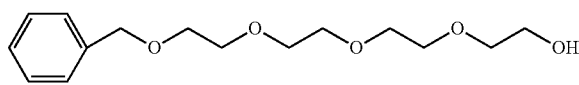

C$_{15}$H$_{24}$O$_5$
Exact Mass: 284.16
Mol. Wt.: 284.35
C, 63.36; H, 8.51; O, 28.13

Potassium t-butoxide (123.8 g, 1.1 moles) was placed into a 3 L flask under argon. Dry THF (10 was added. Dry tetraethylene glycol (tetraEG, 231.2 g, 1.19 moles) was added while maintaining pot temperature below 15° C. There is an exotherm with the release of $H_2$ gas. After 1 h, the pot temperature was at about 15° C., benzyl bromide was added drop wise over about 4 h. Reaction was allowed to stir for 17 h while it warmed to rt. The reaction was monitored by tlc on silica gel plates eluting with 10% MeOH/$CH_2Cl_2$. The benzyl bromide was gone or used up. Reaction mixture was filtered and the filtrate was concentrated in vacuo. The resulting oil was extracted with water (300 mL) and $CH_2Cl_2$ (500 mL); the latter was isolated, dried over $MgSO_4$, filtered and concentrated to an oil. A column was prepared using 600 g silica gel and hexane as needed. The crude product was placed onto column with the same and a minimum TBME (75 mL) was used to make a clean transfer. The column was eluted as follows:

(2 L) hexane; (2 L) 10% TBME/hexane; (4 L) 20% TBME/hexane; (2 L) 30% TBME/hexane; (2 L) 50% TBME/hexane, and (4 L) TBME. Like fraction containing product were combined and concentrated in vacuo to yield an oil that weighs 125.2 g (41%). NMR was consistent with proposed structure. $^1$H NMR[400 MHz, DMSO($d_6$)] □7.35 (m, 5H), 4.58 (t, 1H), 4.48 (s, 2H), 3.59-3.45 (m, 14H), 3.42 (t, 2H), 3.0 (unres(t), 2H).

Example 12

Preparation of 13-(O-benzyl)-1,4,7,10,13-pentaoxapentadecyl)tosylate (PhCH₂O-dPEG₄-OTs)

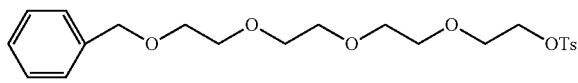

C₂₂H₃₀O₇S
Exact Mass: 438.17
Mol. Wt.: 438.54
C, 60.25; H, 6.90; O, 25.54; S, 7.31

4-O-(benzyl)tetraethylene glycol (72.1 g, 0.25 mole) was placed into a 1 L flask, along with CH₂Cl₂ (650 mL) under argon. TsCl (52.2 g, 0.27 mole) was added, followed by the drop wise addition of Et₃N (40 mL, 0.28 mole). The reaction flask was in an ice; the reaction was stirred for 17 h while allowing it to warm to rt. The reaction was monitored by tlc on silica gel plates eluting with 10% MeOH/CH₂Cl₂. The reaction was tlc, all the PhCH₂O-dPEG₄-OH was consumed. Reaction mixture was filtered, the filtrate was extracted with water (200 mL). The CH₂Cl₂ layer was separated, dried over MgSO₄, filtered and concentrated to an oil. A column was prepared using 600 g silica gel and hexane as needed. The crude product was placed onto column with the same; TBME (75 mL) was used to make a clean transfer. The column was eluted with (2 L) hexane; (4 L) 20% TBME/hexane; (2 L) 30% TBME/hexane; (2 L) 40% TBME/hexane; (2 L) 50% TBME/hexane; (4 L) 20% EtOAc/TBME; (4 L) 50% EtOAc/TBME. Like fraction containing product were combined and concentrated in vacuo to yield an oil that weighs 104.4 g (95%). NMR was consistent with proposed structure. ¹H NMR[400 MHz, DMSO(d₆)] □7.78 (d, 2H), 7.48 (d, 2H), 7.32 [unres(s), 5H], 4.50 (s, 2H), 4.12 (t, 2H) 3.61-3.41 (m, 14H), 2.42 (s, 3H).

Example 13

Preparation of Benzyloctaethylene glycol (BnO-dPEG₈-OH)

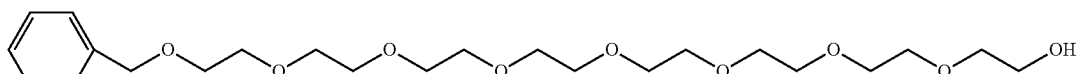

C₂₃H₄₀O₉
Exact Mass: 460.27
Mol. wt.: 460.56
C, 59.98; H, 8.75; O, 31.27

95% Sodium hydride (51.9 g, 2.2 moles) was placed into 5 L flask under argon. Dry THF (2 L) at −20° C. was added. Dry tetraethylene glycol (429.3, 2.21 mole) was placed into a gas venting dropping funnel and added to reaction pot. Make sure that the reaction pot temperature does not exceed 10° C. during the addition. There is an evolution of H₂ gas. When the addition is complete, a homogeneous solution resulted. 18C6 (9.1 g) was added, plus THF (1 L). BnO-dPEG₄OTs (275 g, 0.63 mole) was added slowly over about 3 h, plus THF (500 mL). The reaction mixture was allowed to stir for 17 h while it warmed to rt. The reaction was monitored by tlc on silica gel plates, eluting with 10% MeOH/CH₂Cl₂. The tlc was run on reaction mixture vs BnO-dPEG₄OTs The tlc plates were visualized with aid of UV lamp @ 254 nm. The starting material was converted to the product, so the reaction was worked up. The reaction mixture was filtered and filtrate was concentrated in vacuo; the oil was extracted with brine (700 mL) and 3×500 mL CH₂Cl₂. The CH₂Cl₂ layer was separated, dried over MgSO₄ and filtered. The filtrate was concentrated in vacuo to leave an oil. A column was prepared using silica gel (750 g) and hexane as needed. The crude product was placed onto column with hexane and minimum TMBE (100 mL) to make a clean transfer. The column was eluted as follows: (4 L) hexane; (4 L) 20% TBME/hexane; (2 L) 30% TBME/hexane; (4 L) 50% TBME/hexane; (4 L) TBME; (2 L) 10% EtOAc/TBME; (2 L) 20% EtOAc/TBME. Like fractions containing product were combined to give a yield of 233.5 g (81%). Product was characterized by nmr. ¹H NMR[400 MHz, DMSO(d₆)] □7.35-7.25 (m, 5H), 4.57 (t, 1H), 4.90 (s, 2H), 3.60-3.45 (m, 30H), 3.42 (t, 2H).

Example 14

Preparation of octaethylene glycol (HO-dPEG₈-OH)

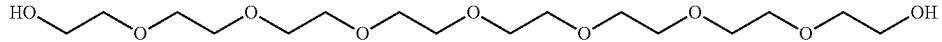

C₁₆H₃₄O₉
Exact Mass; 370.22
Mol. Wt.: 370.44
C, 51.88; H, 9.25; O, 38.87

10% Pd/C (11.2 g) was added to MeOH (50 mL) at −15° C. in hydrogenation bottle under agron. BnO-dPEG₅-OH (69.0 g, 0.15 mole) was added to the bottle along with MeOH (150 mL). The bottle was placed on the Parr shaker for 17 h at 50 psi of H₂. The reaction was monitored by tlc on silica gel plates, eluting with 10% MeOH/CH₂Cl₂. The reaction is about 50% complete. The reaction was worked up. The reaction mixture was filter through glass fiber, used MeOH as needed to make a clean transfer. The filtrate was concentrated in vacuo to give an oil. A column was prepared with 600 g of silica gel and hexane. The crude product was placed onto column with hexane and minimum of TBME (100 mL). The column was eluted as follows: (2 L) 20% TBME/hexane; (2 L) 50% TBME/hexane; (4 L) TBME; (2 L) 5% MeOH/TBME; (2 L) 10% MeOH/TBME. Like fractions containing product were combined and concentrated in vacuo to give 28.5 g (51% yield). The product was characterized by nmr. $^1$H NMR[400 MHz, CDCl$_3$] □4.60 (t, 2H), 3.57-3.50 (m, 28H), 3.45 (t, 4H). Purity is 100% by quantitative nmr, internal std is: bis-(1,4-trichloromethyl)benzene.

Example 15

Preparation of 18-methoxy-1,4,7,10,13,16-hexaoxaoctadecanol (m-dPEG$_6$-OH)

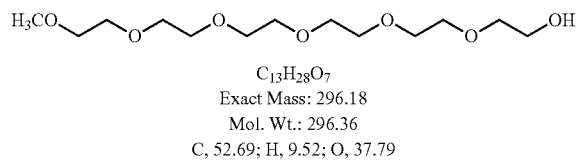 [SMILES: COCCOCCOCCOCCOCCOCCO]

C$_{13}$H$_{28}$O$_7$
Exact Mass: 296.18
Mol. Wt.: 296.36
C, 52.69; H, 9.52; O, 37.79

95% Sodium hydride (46.5 g, 1.8 moles) was placed into 3 L flask under argon. Dry THF (1.1 L) at −20° C. was added to the reaction flask. Dry triethylene glycol (307.7 g, 2.0 moles) was poured into a gas venting dropping funnel and it was added slowly to reaction pot. Do not allow the reaction pot temperature to exceed 10° C. during the addition. There is an evolution of H$_2$ gas. When the addition is complete, a homogeneous solution resulted. Then 9-methoxy-1,4,7-trioxanonayl tosylate, [CH$_3$O-dPEG$_3$-OTs], was dissolved in THF (100 mL) drop wise over approximately 20 minutes. The reaction was stirred at rt for 2 h. Then, the reaction pot temperature was maintained at 37° C. for 17 h with vigorous stirring. The reaction was monitored by tlc on silica gel plates, eluting with 10% MeOH/CH$_2$Cl$_2$ vs starting material. The tlc plates were visualized with aid of UV lamp @ 254 nm and with iodine. Reaction mixture was filtered; the filtrate was extracted with CH$_2$Cl$_2$ (3×700 mL) and water (700 mL). The CH$_2$Cl$_2$ layer was isolated, dried over MgSO$_4$ and filtered. The filtrate was concentrated in vacuo to leave an oil. A column was prepared using silica gel (700 g) and hexane as needed. The crude product was pre-absorbed on 300 g of silica gel and placed onto column with hexane as needed and minimum TMBE (100 mL) to make a clean transfer. The column was eluted as follows: (6 L) hexane; (4 L) 20% TBME/hexane; (3 L) 30% TBME/hexane; (3 L) 40% TBME/hexane; (3 L) 50% TBME/hexane; (3 L) 60% TBME/hexane; (3 L) 80% TBME/hexane; (6 L) TBME; (4 L) 10% MeOH/TBME; (4 L) 20% MeOH/TBME. Like fractions containing product were combined to give a yield of 261.8 g (75%). Product was characterized by nmr. $^1$H NMR[400 MHz, DMSO(d$_6$)] □4.53 (t, 1H), 3.55-3.48 (m, 20H), 4.45-3.42 (s, 4H), 3.24 (2, 3H).
Comments:

The m-dPEG$_6$-OH can be elongated further by converting it to the tosylate, m-dPEG$_6$-OTs. The tosyl group can be displaced a mono-protected dPEG$_n$ alkoxide of choice or in the presence of an excess of the sodium-O-dPEG$_n$-OH of choice. See the scheme below.

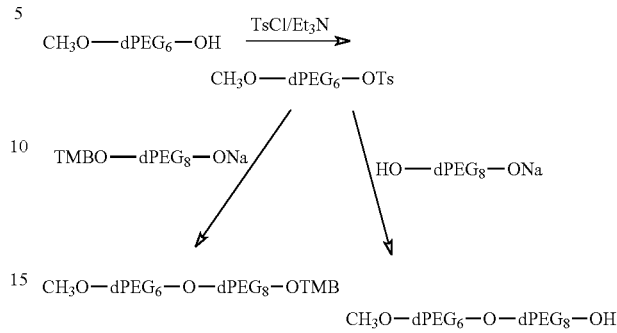

This sequence of reaction can be repeated indefinitely to higher and higher homologues of m-dPEG$_n$ of choice.

Example 16

Preparation of Thio-dPEG$_4$ Acid

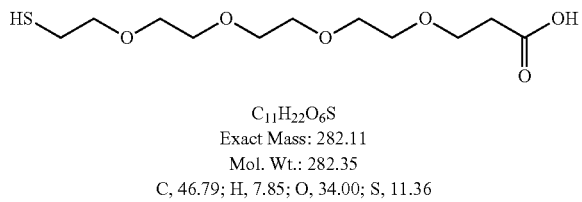 [SMILES: O=C(O)CCOCCOCCOCCOCCS]

C$_{11}$H$_{22}$O$_6$S
Exact Mass: 282.11
Mol. Wt.: 282.35
C, 46.79; H, 7.85; O, 34.00; S, 11.36

TsO-dPEG$_4$CO$_2$-t-bu (185.1 g, 0.43 mole) was placed into 1 L flask along with EtOH (150 mL) and thiourea (38.2 g, 0.50 mole). This mixture was heated under reflux and argon for 17 h. The reaction was monitored by tlc on silica gel plates eluting with 10% MeOH/CH$_2$Cl$_2$. The reaction was complete; the starting material was used up. NaOH pellets (38.2 g, 0.95 mole) was added to pot plus water (100 mL). The reaction was heated under reflux for 2 h. The aqueous layer was cooled to about 5° C. and maintained while bring the pH to 4. The aqueous layer was extracted with CH$_2$Cl$_2$ (3×150 mL), the latter was dried over MgSO$_4$, filtered and concentrated in vacuo to an oil (42.0 g). A column was prepared using 600 g silica gel and hexane.

The crude product was placed on the column with hexane and minimum of TBME (50 mL). The column was flashed with hexane (6 L), and then as follows: (4 L) 30% TBME/hexane; (4 L) 50% TBME/hexane; (4 L) TBME; (2 L) 5% MeOH/TBME; (4 L) 10% MeOH/TBME. Like fractions containing product were combined to give a yield 17.4 g. Product was characterized by nmr. $^1$H NMR[400 MHz, DMSO(d$_6$)] □8.8 (b(s), 1H), 3.77 (t, 2H), 3.63-3.53 (m, 14H), 2.75-2.55 (m, 4H), 1.5 (t, 1H). Purity is 98.5% by quantitative nmr. Internal std is: bis-(1,4-trichloromethyl)benzene.

Example 17

Preparation of Dodecaethylene glycol
(HO-dPEG$_{12}$-OH)

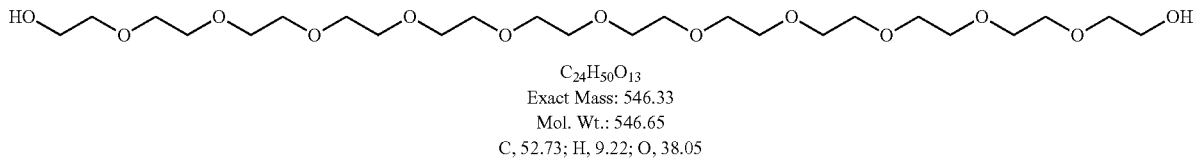 [SMILES: OCCOCCOCCOCCOCCOCCOCCOCCOCCOCCOCCOCCO]

C$_{24}$H$_{50}$O$_{13}$
Exact Mass: 546.33
Mol. Wt.: 546.65
C, 52.73; H, 9.22; O, 38.05

Dodecaethylene glycol is prepared via the bis-O-Bn-dPEG$_{12}$ (BnO-dPEG$_{12}$-OBn). 95% NaH (20.0 g, 0.83 mole) was placed into 3 L flask along with dry THF (800 mL) at about −15° C. under argon with stirring. 18C6 (15.3 g) was added, followed by the addition of BnO-dPEG$_4$-OH (229.0 g, 0.80 mole) dissolved in THF (150 mL) over about 3 h. There was an evolution of hydrogen gas with a slight exotherm. Keep the pot temperature between 15 and 20 C. Once the evolution of hydrogen cease, TsO-dPEG$_4$OTs (200.8 g, 0.40 mole) dissolved in THF (400 mL) was added dropwise over 4 h while cooling the reaction flask in an ice bath. This mixture was stirred under argon while allowing the pot to come to rt overnight (17 h). The reaction was monitored by tlc on silica gel plates eluting with 47% TBME/47% CH$_2$Cl$_2$/6% MeOH. The reaction was complete by tlc; the starting material was used up. Water (500 mL) was added with caution to avoid foaming; THF was removed in vacuo. The aqueous residue was extracted 2×300 mL, then 1×300 mL TBME and finally 2×500 mL CH$_2$Cl$_2$. The product is in the CH$_2$Cl$_2$ layer. The latter was dried over MgSO$_4$, filtered and concentrated in vacuo to give a pure product by tlc vs the authentic material (274.0 g, 47%), BnO-dPEG$_{12}$-OBn.

10% Pd/C (15.7 g) was suspended in MeOH (150 mL) at about −15 C under argon, and placed into calorimeter along with BnO-dPEG$_{12}$-OBn (274 g, 0.38 mole) and MeOH (700 mL). Argon was bubbled through the reaction mixture and the calorimeter was placed on the hydrogenation apparatus, hydrogen was added to 1200 psi and heated at 150 C for 1 h. Then, the reaction was allowed to stir at 1200 psi while the temperature was allowed to fall to rt on its own accord over 17 h. At then end of 17 h, another tlc was run on silica gel plates eluting with 10% MeOH/CH$_2$Cl$_2$. The reaction was complete. Argon was bubbled through the reaction mixture prior to filtering through glass fiber, used MeOH as needed to make a clean transfer. The filtrate was concentrated in vacuo to an oil. The latter was cooled to about −20 C, a solid formed. TBME (1 L) was added and the white solid was broken up and filtered while cool (0 C). The product was dried in vacuo at about 0.01 mm Hg @ rt. The dried product weighs 96.6 g, 46% yield. Nmr is consistent with proposed structure. $^1$H NMR[400 MHz, CDCl$_3$] ☐3.69 (s, 48H), 2.82 (b(s), 2H).

Example 18

Preparation of O-Benzyl dodecaethylene glycol
(BnO-dPEG$_{12}$-OH)

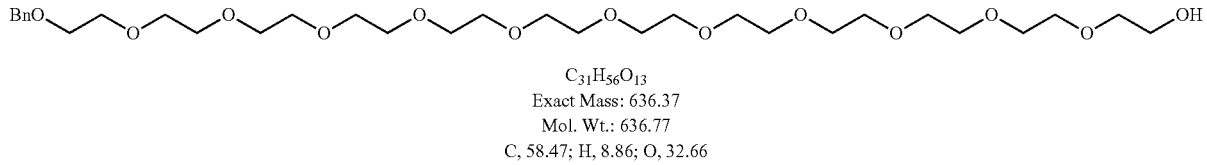 [SMILES: OCCOCCOCCOCCOCCOCCOCCOCCOCCOCCOCCOCCOCc1ccccc1]

C$_{31}$H$_{56}$O$_{13}$
Exact Mass: 636.37
Mol. Wt.: 636.77
C, 58.47; H, 8.86; O, 32.66

95% NaH (14.7 g, 0.61 mole) was placed into 5 L flask along with dry THF (2 L) at about 0 to 5 C under argon with stirring. 18C6 (23.4 g) was added, followed by the addition of HO-dPEG$_{12}$-OH (298.6 g, 0.54 mole) as a solid over about 1 h. There was an evolution of hydrogen gas and no noticeable exotherm to any degree. Keep the pot temperature between 15 and 20 C. Once all the dodecaethylene glycol had been added, benzyl chloride (67 mL, 60.9 g, 0.48 mole) was dissolved in THF (400 mL) and added dropwise over 4 h. Add THF (600 mL). The reaction mixture was allowed to stirring for 17 h while cooling in an ice bath. A tlc was run on silica gel plates, eluting with 10% MeOH/CH$_2$Cl$_2$. The reaction was complete by tlc; no benzyl chloride was presence. Water (150 mL) was added to pot and THF was removed in vacuo. Aqueous saturated NaCl solution (300 mL) was added and extracted with CH$_2$Cl$_2$ (2×400 mL). The latter was dried over MgSO$_4$, filtered and concentrated in vacuo to an oil. A column was prepared with silica gel (600 g) and hexane (6 L). The crude product was pre-absorbed on silica gel (400 g) and placed onto the column. The column was flashed with hexane (6 L), and then by gravity as follows: (2 L) 20% TBME/hexane; (2 L) 30% TBME/hexane; (2 L) 40% TBME/hexane; (2 L) 50% TBME/hexane; (2 L) 60% TBME/hexane; (2 L) 70% TBME/hexane; (2 L) 80% TBME/hexane; (6 L) TBME; (2 L) 1% MeOH/TBME; (2 L) 2% MeOH/TBME; 5% MeOH/TBME; 10% MeOH/TBME; 20% MeOH/TBME. Like fractions containing product were combined to give a yield of 85.6 g (25%). TLC consistent with authentic material.

Example 19

Preparation of Dotriacontanohexaethylene glycol
(HO-dPEG₃₆-OH)

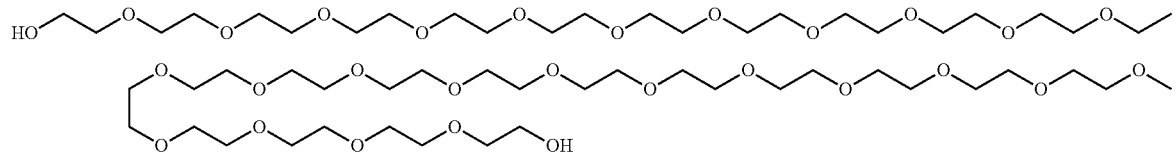

C₇₂H₁₄₆O₃₇
Exact Mass: 1602.95
Mol. Wt.: 1603.91
C, 53.92; H, 9.18; O, 36.91

95% NaH (5.2 g, 0.22 mole) was placed into 3 L flask along with dry THF (1 L) at about 0 to 5 C under argon with stirring. 18C6 (10 g) was added, followed by the addition of BnO-dPEG$_{12}$-OH (85.1 g, 0.13 mole). Keep the pot temperature between 15 and 20 C. After 15 minutes, TsO-dPEG$_{12}$-OTs (55.0 g, 0.06 mole) was added. The reaction mixture was allowed to stirring for 17 h while cooling in an ice bath. A tlc was run on silica gel plates, eluting with 10% MeOH/CH$_2$Cl$_2$. All the bis-tosylate was consumed. MeOH (100 mL) was added, followed by water (250 mL), note foaming. THF was removed in vacuo and water (500 mL) was added to pot. The aqueous layer was extracted with hexane (2×300 mL), TBME (2×300 mL), and CH$_2$Cl$_2$ (2×500 mL). The product is in the CH$_2$Cl$_2$ layer. The latter was dried over MgSO$_4$, filtered and concentrated to give an oil (138.2 g, 60%). The BnO-dPEG$_{36}$-OBn was hydrogenated. 10% Pd/C (10 g) was suspended in −15 C MeOH (150 mL) under argon, and placed into calorimeter along with BnO-dPEG$_{36}$-OBn (138.2 g, 7.74×10 mole) and MeOH (600 mL). Argon was bubbled through the reaction mixture and the calorimeter was placed on the hydrogenation apparatus, hydrogen was added to 1400 psi and heated at 150 C for 2 h. The reaction was complete by tlc on silica gel plates eluting with 10% MeOH/CH$_2$Cl$_2$. Argon was bubbled through the rt reaction mixture prior to filtering through glass fiber, used MeOH as needed to make a clean transfer. The filtrate was concentrated in vacuo to give a white solid. The flask was cooled to about −10 C with the addition of TBME (1 L). The solid was broken up and filtered cold to give the desire product on drying in vacuo at rt for 17 h and 0.01 mm Hg. The dried product weighs 95.6 g, 77% yield. The nmr is consistent for the structure. $^1$H NMR[400 MHz, CDCl$_3$ 3.50 (s, 144 H).

Example 20

Preparation of ditosyl-O-dodecaethylene glycol
(TsO-dPEG$_{12}$-OTs)

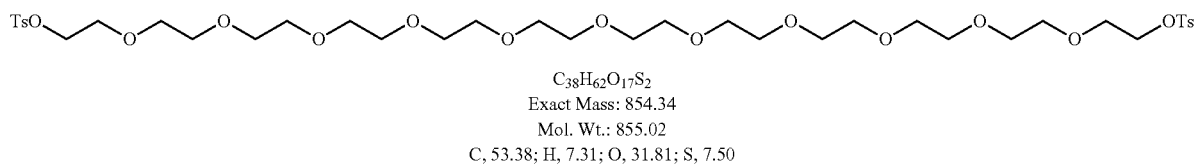 [SMILES: Cc1ccc(S(=O)(=O)OCCOCCOCCOCCOCCOCCOCCOCCOCCOCCOCCOCCOS(=O)(=O)c2ccc(C)cc2)cc1]

C₃₈H₆₂O₁₇S₂
Exact Mass: 854.34
Mol. Wt.: 855.02
C, 53.38; H, 7.31; O, 31.81; S, 7.50

HO-dPEG$_{12}$-OH (96.0 g, 0.17 mole) was dissolved in CH$_2$Cl$_2$ (700 mL) and TsCl (72 g, 0.38 mole) was added along with Et$_3$N (60 mL) under argon while cooling in an ice bath. The reaction was allowed to stir for 17 h while allow it to come to rt on its own accord. The reaction was tlc on silica gel plates while eluting with 10% MeOH/CH$_2$Cl$_2$. The reaction was complete all the dodecaethylene glycol was consumed. The reaction mixture was filter and the filtrate was washed with water (500 mL) and extracted 3×400 mL hexane, and 2×500 mL of CH$_2$Cl$_2$. The latter was dried over MgSO$_4$, filtered, concentrated in vacuo to give an oil that weighs 141.2 g, 97.1% yield. The nmr is consistent with the proposed structure. $^1$H NMR[400 MHz, CDCl$_3$ 7.8 (d, 4H), 7.35 (d, 4H), 4.10 (t, 4H), 3.80-3.50 (m, 44H), 2.45 (s, 6H). Note: TsO-dPEG$_4$-OTs is readily prepared by a similar process.

Example 21

O-THP-33-Methoxy-1,4,7,10,13,16,19,22,25,28,30-undecaoxadotriacontanotriethylene glycol (m-dPEG$_{11}$-OTHP)

$C_{28}H_{56}O_{13}$
Exact Mass: 600.37
Mol. Wt.: 600.74
C, 55.98; H, 9.40; O, 34.62

H$_3$CO-dPEG$_7$-OTs (406.7 g, 0.82 mole) was placed was placed into 5 L flask. THPO-dPEG$_4$OH (238.4 g, 0.86 mole) was added to pot along with THF (1.6 L) and 18C6 (10.5 g). t-BuO$^-$K (95.6 g, 0.85 mole) was dissolved in THF (400 mL) and was added to the pot in a drop wise fashion so as to titrate the reaction mixture over a 3 h period. The reaction solution was allowed to stir at rt for 17 h under argon. The reaction mixture was complete by tlc on silica gel plates, eluting with 10% MeOH/CH$_2$Cl$_2$; all the tosylate was consumed. Water (1 L) was added and the THF was removed in vacuo. The aqueous residue was extracted with TBME (6×700 mL), the extracts were discarded. The aqueous layer was extracted with CH$_2$Cl$_2$ (2×500 mL). The organic extracts were combined and dried over MgSO$_4$, filtered, concentrated in vacuo to an oil. The latter was dried by azeotrope over toluene (200 mL) in vacuo to give 388.1 g (79% yield). The nmr is consistent for the proposed product. $^1$H NMR[400 MHz, CDCl$_3$ ☐☐6.5 (b(t), 1H), 3.82-3.95 (m, 2H), 3.48-3.78 (m, 44H), 3.37 (s, 3H), 1.89-1.40 (m, 6H).

Example 22

33-Methoxy-1,4,7,10,13,16,19,22,25,28,30-undecaoxadotriacontanotriethylene glycol

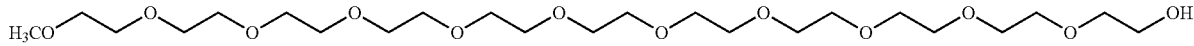

$C_{23}H_{48}O_{12}$
Exact Mass: 516.31
Mol. Wt.: 516.62
C, 53.47; H, 9.36; O, 37.16 m-dPEG$_{11}$-OTHP (385 g, 0.64 mole) was placed into 3 L flask along with MeOH (1 L) and pyridinium toluenesulfonic acid (6 g). The reaction solution was heated under argon at 53 C for 2.5 h. A tlc was run, eluting with 10% MeOH/CH$_2$Cl$_2$; the reaction was complete all the starting material (m-dPEG$_{11}$-OTHP) was consumed. The MeOH was removed in vacuo to leave an oil. 50% (aq) NaOH solution was added along with water (700 mL). The aqueous reaction solution was extracted with TBME (3×500 mL), then with CH$_2$Cl$_2$ (3×500 mL). The CH$_2$Cl$_2$ extracts were combined and dried over MgSO$_4$, filtered and concentrated in vacuo to give 310 g (94% yield); same as the authentic material by tlc.

Example 23

Preparation of THP-dPEG$_4$-OH

To a 3 liter round bottom flask, equipped with an overhead stirrer is added neat, 1200 g of tetraethylene glycol and 430 g of dihydropyran. To this is added 20 drops of conc. HCl over about 4 hours, then let stir overnight. 10 g of powdered potassium carbonate is added and let dissolve. The reaction mixture is diluted with 2 l of water and extracted 6×500 ml of t-butyl methyl ether. The combined ether extracts are washed with about 500 ml of water and the latter is added to the first aqueous portion. The water is extracted with 4×500 ml portions of methylene chloride, which are combined and dried with sodium sulfate. The methylene chloride is removed under pressure and the product is dried azeotropically with toluene to yield 830 g of pure product (58%).

Example 24

Preparation of THP-dPEG$_{12}$-OTHP (Stepwise Method—Titration of Potassium t-Butoxide)

A solution is prepared under an inert atmosphere containing 570 g of the bis-dPEG$_4$-OTs and 650 g of the mono-THP-dPEG$_4$-OH in about 2.5 l of dry THF. To this solution is added dropwise over a period of 2 h a freshly prepared solution of potassium t-butoxide in THF (270 g in 1 l of dry THF). The reaction is complete and the temperature is kept below 30° C. throughout. To this slurry is added 1.5 l of water to give a homogeneous solution from which the THF is removed under vacuum. The aqueous solution containing the product is washed with 3×1 l of TBME, then the product is extracted with 2×1.5 l of methylene chloride. The methylene chloride is dried over Na$_2$SO$_4$ and removed under vacuum, leaving 750 g of pure product as determined by $^1$H NMR and chromatography.

Example 25

Preparation of N₃-dPEG₁₂-OTHP 18.9 g (0.788 mole) of sodium hydride (dry, 95%) is weighed into a 3 liter round bottom under argon, to which is added 500 ml of dry THF and 10 g of 18-crown-6. This slurry is cooled with an ice bath and a 50% v/v solution of the THP-dPEG4-OH (175 g; 0.629 moles) is added dropwise over about 2 h, with stirring continued for another 4 h. Then a 50% v/v THF solution of the N3-dPEG8-OTs (315 g; 0.574 moles) to the cooled slurry this is added over 1 h. The slurry is stirred overnight while the reaction comes to ambient. About 100 ml of a 10% aqueous THF solution is added carefully to quench any excess sodium hydride, followed by enough water to dissolve all of the salt by-products. The solution shows by TLC to be only one new product plus the excess THP-dPEG4-OH. The THF is removed under vacuum, diluted to a final volume of 1.5 l of water. The product is extracted 4×500 ml with methylene chloride and the combined organic extracts washed with 3×500 ml of a dilute sodium bicarbonate solution. The methylene chloride solution is dried with sodium sulfate. The product mixture is taken up in about 500 ml of methanol with 5 grams of p-toluene sulfonic acid and stirred at room temperature for 2 h. TLC shows complete disappearance of both THP derivatives. The methanol is removed under vacuum, taken up in 1 liter of methylene chloride, washed 2×250 ml 5% brine (to remove the tetraethylene glycol, product of deprotection of the excess THP-dPEG4-OH used), and dried over sodium sulfate. The product further purified on silica gel using hexanes, TBME and methanol as elution solvents to yield 240 g (73%) of product.

We claim:

1. A method for selectively making specific discrete (polyethylene glycol) (dPEG) compounds containing a discrete and predetermined number of ethylene oxide moieties, which comprises the steps of:
   (a) forming a reaction mixture comprising a first dPEG compound having the general structural formula I or I':

$$R^1\text{-}d\text{PEG}_x\text{-OH} \qquad \qquad \text{I}$$

$$R^1\text{-}d\text{PEG}_x\text{-OR}^2 \qquad \qquad \text{I'}$$

and a dPEG compound having the structural formula X or X', respectively:

$$R^3\text{-}d\text{PEG}_y\text{-OR}^2 \qquad \qquad \text{X}$$

$$R^3\text{-}d\text{PEG}_y\text{-OH} \qquad \qquad \text{X'}$$

(b) adding a non-sodium ionizing agent, which is potassium t-butoxide, in the presence of a catalyst and under conditions to produce a dPEG compound having the structural formula XI $$R^1\text{-}d\text{PEG}_{x+y}\text{-}R^3 \qquad \qquad \text{XI;}$$

wherein said potassium t-butoxide ionizing compound is added to a reaction mixture of compounds I and X and II, or I' and X', at a rate that is about equal to the rate at which compound XXII formed in situ from compound I reacts with compound X or the rate at which compound XXII" formed in situ from compound I' reacts with compound X', respectively, wherein:

$$R^1\text{-}d\text{PEG}_x\text{-O}^-\text{M}^+ \qquad \qquad \text{XXII}$$

$$R^3\text{-}d\text{PEG}_y\text{-O}^-\text{M}^+ \qquad \qquad \text{XXII',}$$

wherein, $R^1$ and $R^3$ each independently are one or more of a hydroxy protecting group (PG), a functional group (FG), or a protected functional group; $R^2$ is a leaving group, x ranges from about 1 to 300, and y ranges from about 1 to 300.

2. The method of claim 1, which comprises the additional step of:
   (c) one or more of selectively removing $R^1$ in the presence of $R^3$ or selectively removing $R^3$ in the presence of $R^1$, to produce compounds of formulas XII and XIII, respectively, $$\text{HO-}d\text{PEG}_{x+y}\text{-}R^3 \qquad \qquad \text{XII}$$

$$R^1\text{-}d\text{PEG}_{x+y}\text{-OH} \qquad \qquad \text{XIII.}$$

3. The method of claim 1, wherein said ionizing agent is one or more of potassium t-butoxide, potassium hydride, n-butyl lithium, t-butyl lithium, or lithium diisopropylamine.

4. The method of claim 1, wherein a portion of $d\text{PEG}_y$ or $d\text{PEG}_x$ is partially replaced with X, which is an aliphatic, aromatic, or aliphatic-aromatic organic linker moiety optionally substituted with heteroatoms.

5. The method of claim 1, wherein said reactants are dispersed in a solvent.

6. The method of claim 5, wherein said solvent is one or more of tetrahydrofuran (THF), toluene, dioxane, trichloroethylene, or tetrachloroethylene.

7. The method of claim 1, where $R^1$ and $R^3$ both are PG groups, and further comprising one or more of $R^1$ of compound XII or $R^3$ of compound XIII is removed to produce a compound of formula XIV:

$$\text{HO-}d\text{PEG}_{2x+y}\text{-R} \qquad \qquad \text{XIV}$$

where, R is $R^1$ or $R^3$.

8. The method of claim 7, wherein compound XIV is converted to a compound of formula V':

$$R\text{-}d\text{PEG}_{2x+y}\text{-OR}^2 \qquad \qquad \text{V.}$$

9. The method of claim 8, further comprising:
   forming a reaction mixture comprising said dPEG compound V or XVIII and a dPEG compound having the structure of formula V' or XVIII', respectively, where:

$$R^5\text{-}d\text{PEG}_z\text{-OH} \qquad \qquad \text{XVIII}$$

$$R^5\text{-}d\text{PEG}_z\text{-OR}^2 \qquad \qquad \text{XVIII'}$$

$$R\text{-}d\text{PEG}_{2x+y}\text{-OH} \qquad \qquad \text{V'}$$

adding an ionizing agent optionally in the presence of a catalyst and under conditions to produce a dPEG compound having the structural formula VI $$R^5\text{-}d\text{PEG}_{2x+y+z}\text{-R} \qquad \qquad \text{VI}$$

wherein z is 1 to 300, $R^5$ is a PG or FG, and $R^2$ is a leaving group.

10. The method of claim 1, wherein the molar ratio of compound I to compound X, or compound I' to compound X', is between about 1:1 and about 1.05:1.

11. The method of claim 9, wherein the molar ratio of compound XVIII to compound VI is between about 1:1 and about 1.05:1.

12. The method of claim 1, wherein the purity of compound XI produced is greater than about 98%.

13. The method of claim 9, where $R^1$ or $R^3$ is a PG group, and further comprising R or $R^5$ of compound VI is removed produce a compound of formula VII or XXIX, respectively:

$$R^5\text{-}d\text{PEG}_{2x+y+z}\text{-OH} \qquad \qquad \text{VII}$$

$$R\text{-}d\text{PEG}_{2x+y+z}\text{-OH} \qquad \qquad \text{XXIX.}$$

14. The method of claim 1, which includes a catalyst to promote the complexation of $M^+$.

15. The method of claim 9, which includes a catalyst to promote the complexation of $M^+$.

16. The method of claim 15, wherein said catalyst is a cryptand catalyst.

17. The method of claim 16, wherein said catalyst is one or more of 18-crown-6 or a derivative of 18-crown-6.

18. The method of claim 1, wherein $R^1$ or $R^3$ is a functional group.

19. The method of claim 9, wherein $R^1$ or $R^5$ is a functional group.

20. The method of claim 18, wherein $R^1$ or $R^3$ is one or more of a protected amine, a nitrile group, an alkoxy group, an aryloxy group, a protected thiol group, or a protected carboxyl group.

21. The method of claim 19, wherein $R^1$ or $R^5$ is one or more of a protected amine, a nitrile group, an alkoxy group, an aryloxy group, a protected thiol group or a protected carboxyl group.

22. The method of claim 20, wherein said protected amine is one or more of an azido group, a trityl, a substituted trityl, a phthalimido group, CBZ, t-boc, benzyl group, a substituted benzyl group.

23. The method of claim 21, wherein said protected amine is one or more of an azido group, CBZ, t-boc, benzyl group, a substituted benzyl group, a phthalimido group, trityl, or a substituted trityl.

24. The method of claim 22, wherein said protected amine is an azido group, which is subsequently reduced to an amine group with triphenyl phosphine.

25. The method of claim 23, wherein said protected amine is an azido group, which is subsequently reduced to an amine group with triphenyl phosphine.

26. The method of claim 20, wherein said thiol group is protected with one or more of an aralkyl group, an acetyl group, a trityl group, a substituted trityl group, or a thiourea group.

27. The method of claim 21, wherein said thiol group is protected with one or more of an aralkyl group, an acetyl group, a trityl group, a substituted trityl group, or a thiourea group.

28. The method of claim 8, wherein R in compound V is converted into one or more of an OH group, an ester group, a carboxyl group, an amine group, or a thiol group.

29. The method of claim 1, wherein $R^1$ or $R^3$ in compound XI is a protective group that is subsequently removed under acidic conditions.

30. The method of claim 9, wherein $R^1$ or $R^5$ in compound VI is a protective group that is subsequently removed under acidic conditions.

31. The method of claim 29, wherein said acidic conditions include the use of one or more of tetrahyropyran-2-yl (THP), TMB (2,4,6-trimethylbenzyl), 4-alkoxybenzyl-, 3,4-dialkoxybenzyl, 4-aralkylxoxybenzyl-, 3,4-diaralkyloxybenzyl-, trityl, or a substituted trityl.

32. The method of claim 29, wherein $R^1$ or $R^3$ is one or more of tetrahyropyran-2-yl (THP), TMB (2,4,6-trimethylbenzyl), 4-alkoxybenzyl-, 3,4-dialkoxybenzyl, 4-aralkylxoxybenzyl-, 3,4-diaralkyloxybenzyl-, trityl, or a substituted trityl.

33. The method of claim 1, wherein $R^1$ or $R^3$ in structure XI is a protective group that is subsequently removed under reducing conditions.

34. The method of claim 33, wherein said reducing conditions comprise one or more of a metal catalyst and hydrogen or a Raney/Ni reducing system.

35. The method of claim 33, wherein $R^1$ or $R^3$ is one or more of benzyl, TMB, PMB and p-alkoxybenzyl, DMB, 3,4-dialkoxybenzyl, 4-aralkylxoxybenzyl, or 3,4-diaralkyloxybenzyl.

36. The method of claim 34, wherein said reducing conditions comprise a Raney/Ni reducing system, and $R^1$ or $R^3$ is one or more of benzyl, TMB, PMB and p-alkoxybenzyl, DMB, 3,4-dialkoxybenzyl, 4-aralkylxoxybenzyl, or 3,4-diaralkyloxybenzyl.

37. The method of claim 1, wherein $R^1$ or $R^3$ in structure XI is a protective group that is subsequently removed in the presence of one or more of DDQ or cerium ammonium nitrate.

38. The method of claim 37, wherein $R^1$ or $R^3$ is one or more of p-alkoxybenzyl 3,4-dialkoxybenzyl, 4-aralkylxoxybenzyl, or 3,4-diaralkyloxybenzyl protecting groups, where the alkyl of the alkoxy ranges from $C_1$-$C_{22}$.

39. A method for selectively making specific discrete (polyethylene glycol) (dPEG) compounds containing a discrete and predetermined number of ethylene oxide moieties, which comprises the steps of:

(a) forming a reaction mixture comprising:

(i) a first reactant having the general structural formula XXVI $$R^1\text{—}X\text{—}(OH)_p \qquad \text{XXVI}$$

and a second dPEG compound having the general structural formula X $$R^3\text{-}d\text{PEG}_y\text{-}OR^2 \qquad \text{X}$$

or (ii) a third reactant having the general structural formula XVII $$R^1\text{—}X\text{—}(R^2)_p \qquad \text{XVII}$$

and a fourth dPEG compound having the general structural formula XVIII $$R^3\text{-}d\text{PEG}_y\text{-}OH \qquad \text{XVIII}$$

(b) adding a non-sodium ionizing compound, which is potassium t-butoxide, to said reaction mixture under reaction conditions comprising a catalyst to produce a dPEG compound having the general structural formula XXVII $$R^1\text{—}X\text{—}(O\text{-}d\text{PEG}_yR^3)_p \qquad \text{XXVII}$$

wherein said ionizing compound is added to a reaction mixture at a rate that is about equal to the rate at which compound XXVI reacts with compound X or compound XVII reacts with compound XVIII, wherein, dPEG represents a discrete ($OCH_2CH_2$) moiety, each $R^1$ independently is a functional group (FG), a protected functional group, or a protecting group (PG); y ranges from about 1 to 1000; $R^2$ is a leaving group; each $R^3$ independently is a functional group (FG), a protected functional group, or a protecting group (PG); $R^1$ and $R^3$ are different; y ranges from about 1 to 1000; p ranges from about 2 to 9; and X is dPEG, an aliphatic, aromatic, aliphatic-aromatic organic linker moiety optionally substituted with heteroatoms.

40. The method of claim 39, wherein p ranges from 2 to 4.

41. The method of claim 39, wherein said ionizing compound is one or more of potassium t-butoxide, potassium hydride, n-butyl lithium, t-butyl lithium, or lithium diisopropylamine.

42. The method of claim 39, wherein said reactants are dispersed in a solvent.

43. The method of claim 42, wherein said solvent is one or more of tetrahydrofuran (THF), toluene, dioxane, trichloroethylene, or tetrachloroethylene.

44. The method of claim 39, where $R^1$ and $R^3$ both are PG groups, and further comprising one or more of $R^1$ of compound XXVII is removed to produce the hydroxy containing compound, which is reacted with $$R^1\text{—}X'\text{—}(R^2)_{p'} \qquad \text{XX}$$

in the presence of an ionizing agent to produce:

$$R^1\text{—}X'\text{—}(\text{—}X\text{—}(O\text{-}dPEG_yR^3)_p)_{p'} \qquad \text{XXI}$$

where p' ranges from about 2 to 9, and X' is dPEG, an aliphatic, aromatic, aliphatic-aromatic organic linker moiety optionally substituted with heteroatoms.

45. The method of claim 44, further comprising deprotecting $R^1$ from compound XXI to produce compound XXX, which is reacted with compound XXVI to produce compound XXXI, as follows:

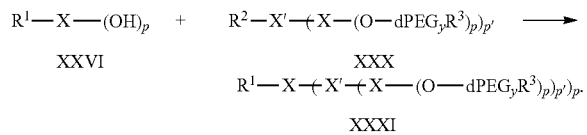

46. The method of claim 45, further comprising converting compound XXXI into one or more of:

$$R^1\text{—}X'\text{—}(\text{—}X\text{—}(O\text{-}dPEG_yT)_p)_{p'} \qquad \text{XXXII}$$

or $$R^1\text{—}X\text{—}(\text{—}X'\text{—}(\text{—}X\text{—}(O\text{-}dPEG_yT)_p)_{p'})_p \qquad \text{XXXIII}$$

where T is a biologically active compound.

47. The method of claim 46, further comprising one or more of $R^1$ in compounds XXI and XXXI being selectively removed and converted to a functional group or where $R^1$ is a functional group which are reactable with T may be converted to branched compounds XXXIV and XXXV:

$$T\text{-}X'\text{—}(\text{—}X\text{—}(O\text{-}dPEG_yR^3)_p)_{p'} \qquad \text{XXXIV}$$

$$T\text{-}X\text{—}(\text{—}X'\text{—}(\text{—}X\text{—}(O\text{-}dPEG_yR^3)_p)_{p'})_p \qquad \text{XXXV}$$

48. The method of claim 39, wherein the molar ratio of compound XXVI to compound X is between about 1:p.

49. The method of claim 44, wherein the molar ratio of compound XX to compound X is between about 1:p.

50. The method of claim 44, wherein the purity of compound XXI produced is greater than about 95%.

51. The method of claim 39, which includes a catalyst to promote the complexation of $M^+$.

52. The method of claim 44, which includes a catalyst to promote the complexation of $M^+$.

53. The method of claim 52, wherein said catalyst is a cryptand catalyst.

54. The method of claim 53, wherein said catalyst is one or more of 18-crown-6 or a derivative of 18-crown-6.

55. The method of claim 39, wherein $R^1$ or $R^3$ is a functional group.

56. The method of claim 44, wherein $R^1$ or $R^3$ is a functional group.

57. The method of claim 55, wherein $R^1$ or $R^3$ is one or more of a protected amine, a nitrile group, an alkoxy group, an aryloxy group, a carboxyl group, or a protected thiol group.

58. The method of claim 57, wherein said protected amine is one or more of an azido group, CBZ, t-boc, benzyl group, a substituted benzyl group, a phthalimido group, a trityl, or a substituted trityl.

59. The method of claim 58, wherein said protected amine is one or more of an azido group, CBZ, t-boc, benzyl group, a substituted benzyl group, a phthalimido group, a trityl, or an alkoxysubstituted trityl.

60. The method of claim 58, wherein said protected amine is one or more of an azido group, CBZ, t-boc, benzyl group, a substituted benzyl group, trityl, or a substituted trityl.

61. The method of claim 57, wherein said protected amine is an azido group, which is subsequently reduced to an amine group with triphenyl phosphine.

62. The method of claim 60, wherein said protected amine is an azido group, which is subsequently reduced to an amine group with triphenyl phosphine.

63. The method of claim 57, wherein said carboxyl group is protected with one or more of an alkyl group or an aralkyl group.

64. The method of claim 57, wherein said protecting group is one or more of a t-butyl group or a benzyl group.

65. The method of claim 58, wherein said carboxyl group is protected with one or more of an alkyl group or an aralkyl group.

66. The method of claim 65, wherein said protecting group is one or more of a t-butyl group or a benzyl group.

67. The method of claim 57, wherein said thiol group is protected with one or more of an aralkyl group, an acetyl group, a trityl, a substituted trityl, or a thiourea group.

68. The method of claim 58, wherein said thiol group is protected with one or more of an aralkyl group, an acetyl group, a trityl, a substituted trityl, or a thiourea group.

69. The method of claim 44, wherein $R^1$ or $R^3$ in compound XXI is converted into one or more of an OH group, an ester group, a carboxyl group, an amine group, or a thiol group.

70. The method of claim 39, wherein $R^1$ or $R^3$ in structure XXVII is a protective group that is subsequently removed under acidic conditions.

71. The method of claim 44, wherein $R^1$ or $R^3$ in structure XXI is a protective group that is subsequently removed under acidic conditions.

72. The method of claim 71, wherein said acidic conditions include the use of one or more of tetrahyropyran-2-yl (THP), TMB (2,4,6-trimethylbenzyl), 4-alkoxybenzyl, 3,4-dialkoxybenzyl, 4-aralkylxoxybenzyl, 3,4-diaralkyloxybenzyl, trityl, or a substituted trityl protecting group.

73. The method of claim 70, wherein $R^1$ or $R^3$ is one or more of tetrahyropyran-2-yl (THP), TMB (2,4,6-trimethylbenzyl), 4-alkoxybenzyl-, 3,4-dialkoxybenzyl, 4-aralkylxoxybenzyl, 3,4-diaralkyloxybenzy-, trityl, or a substituted trityl protecting group.

74. The method of claim 71, wherein $R^1$ or $R^3$ in structure XXVII is a protective group that is subsequently removed under reducing conditions.

75. The method of claim 74, wherein said reducing conditions comprise one or more of a metal catalyst and hydrogen or a Raney/Ni reducing system.

76. The method of claim 74, wherein $R^1$ or $R^3$ is one or more of benzyl, TMB, PMB and p-alkoxybenzyl, DMB, 3,4-dialkoxybenzyl, 4-aralkylxoxybenzyl, or 3,4-diaralkyloxybenzyl.

77. The method of claim 75, wherein said reducing conditions comprise a Raney/Ni reducing system and $R^1$ or $R^3$ is one or more of benzyl, TMB, PMB and p-alkoxybenzyl, DMB, 3,4-dialkoxybenzyl, 4-aralkylxoxybenzyl, or 3,4-diaralkyloxybenzyl.

78. The method of claim 44, wherein $R^1$ or $R^3$ in structure XXI is a protective group that is subsequently removed in the presence of one or more of DDQ or cerium ammonium nitrate.

79. The method of claim 78, wherein $R^1$ or $R^3$ is one or more of p-alkoxybenzyl, 3,4-dialkoxybenzyl, p-aralkoxybenzyl, or 3,4-diaralkoxybenzyl protecting groups, where the alkyl of the alkoxy ranges from $C_1$-$C_{22}$.

* * * * *